(12) United States Patent
Roberts et al.

(10) Patent No.: US 6,194,441 B1
(45) Date of Patent: Feb. 27, 2001

(54) OXAZOLIDINONE DERIVATIVES AND THEIR USE AS ANTIBACTERIAL AGENTS

(75) Inventors: David Anthony Roberts; Michael John Betts, both of Macclesfield (GB)

(73) Assignee: Zeneca Ltd. (GB)

( * ) Notice: Subject to any disclaimer, the term of this patent is extended or adjusted under 35 U.S.C. 154(b) by 0 days.

(21) Appl. No.: 09/486,008

(22) PCT Filed: Aug. 18, 1998

(86) PCT No.: PCT/GB98/02477

§ 371 Date: Feb. 18, 2000

§ 102(e) Date: Feb. 18, 2000

(87) PCT Pub. No.: WO99/10343

PCT Pub. Date: Mar. 4, 1999

(30) Foreign Application Priority Data

Aug. 22, 1997 (GB) .................................................. 9717804

(51) Int. Cl.[7] .................. A61K 31/422; A61K 31/4439; C07D 413/10; C07D 413/14
(52) U.S. Cl. ............................ 514/340; 514/63; 514/376; 546/271.4; 548/110; 548/231
(58) Field of Search ................... 548/110, 231; 546/271.4; 514/63, 340, 376

(56) References Cited

U.S. PATENT DOCUMENTS

| | | | |
|---|---|---|---|
| 4,287,351 | 9/1981 | Bourgery et al. | 548/232 |
| 4,346,102 | 8/1982 | Langlois et al. | 424/279 |
| 4,476,136 | 10/1984 | Dostert et al. | 424/272 |
| 4,705,799 | 11/1987 | Gregory | 514/376 |
| 4,942,183 | 7/1990 | Gregory et al. | 514/376 |
| 4,948,801 | 8/1990 | Carlson et al. | 514/307 |
| 4,977,173 | 12/1990 | Brittelli et al. | 514/376 |
| 5,043,443 | 8/1991 | Carlson et al. | 544/112 |
| 5,164,510 | 11/1992 | Brickner | 548/231 |
| 5,182,403 | 1/1993 | Brickner | 548/231 |
| 5,231,188 | 7/1993 | Brickner | 548/221 |
| 5,523,403 | 6/1996 | Barbachyn | 544/137 |
| 5,529,998 | 6/1996 | Häbich et al. | 514/233.8 |
| 5,547,950 | 8/1996 | Hutchinson et al. | 514/252 |
| 5,565,571 | 10/1996 | Barbachyn et al. | 546/144 |
| 5,574,055 | 11/1996 | Borgulya et al. | 514/376 |
| 5,652,238 | 7/1997 | Brickner et al. | 514/235.8 |
| 5,654,428 | 8/1997 | Barbachyn et al. | 544/235 |
| 5,668,286 | 9/1997 | Yamada et al. | 546/209 |
| 5,688,792 | 11/1997 | Barbachyn et al. | 514/235.5 |
| 5,698,574 | 12/1997 | Reidl et al. | 514/376 |
| 5,708,169 | 1/1998 | Hester, Jr. et al. | 549/152 |
| 5,719,154 | 2/1998 | Tucker et al. | 514/252 |
| 5,736,545 | 4/1998 | Gadwood et al. | 514/252 |
| 5,880,118 | 3/1999 | Barbachyn et al. | 514/211 |
| 5,922,708 | 7/1999 | Riedl, et al. | 514/236.8 |
| 5,981,528 | 11/1999 | Gravestock | 514/252 |

FOREIGN PATENT DOCUMENTS

| | | | |
|---|---|---|---|
| 24985/95 | 2/1996 | (AU) | C07J/1/00 |
| 50735/96 | 10/1996 | (AU) | C07D/413/10 |
| 2154024 | 1/1996 | (CA) | C07D/413/04 |
| 0127902 | 12/1984 | (EP) | C07D/263/20 |
| 0184170 | 6/1986 | (EP) | C07D/263/20 |
| 0312000 | 4/1989 | (EP) | C07D/263/20 |
| 0316594 | 5/1989 | (EP) | C07D/263/20 |
| 0352781 | 1/1990 | (EP) | C07D/263/20 |
| 0359418 | 3/1990 | (EP) | C07D/413/04 |
| 0609905 | 8/1994 | (EP) | C07D/413/04 |
| 0657440 | 6/1995 | (EP) | C07D/263/24 |

(List continued on next page.)

OTHER PUBLICATIONS

*Abstracts of the 36th ICAAC(Interscience Congress of Antimicrobial Agents and Chemotherapy)*, New Orleans, pp. 41,52,140, (1996).

Ashtekar, D., et al., "Oxazolidinones, a New Class of Synthetic Antituberculosis Agent: In vitro and in vivo Activities of DuP–721 Against Mycobacterium tuberculosis", *Diagn. Microbiol. Infect. Dis.*, 14, 465–471, (1991).

Barbachyn, M., et al., "Identification of a Novel Oxazolidinone (U–100480) with Potent Antimycobacterial Activity", *J. Medical Chemistry*, 39, 680–685, (1996).

(List continued on next page.)

*Primary Examiner*—Laura L. Stockton
(74) *Attorney, Agent, or Firm*—Richard V. Person

(57) ABSTRACT

The invention concerns a compound of formula (I) wherein for example $R^1$ is of the formula —NHC(=O)$R^a$ wherein $R^a$ is hydrogen, or (1–4C)alkyl; $R^2$ and $R^3$ are independently hydrogen or fluoro, $R^4$ is hydrogen, (1–4C)alkyl, halo or trifluoromethyl; $R^5$ and $R^6$ are, for example, independently hydrogen, (1–4C)alkyl, an acetylene of the formula -≡-H or -≡-(1–4C)alkyl, or a group of formula (IA) wherein, for example, Z is hydrogen or (1–4C)alkyl; X and Y are (1–4C)alkyl, halo, cyano, phenyl or heteroaryl; provided that X, Y and Z do not define a (2–4C)alkenyl group and provided that at least one of $R^5$ and $R^6$ is a group of formula (IA) or an acetylene of the formula -≡-H or -≡-(1–4C) alkyl; and pharmaceutically acceptable salts thereof; processes for their preparation; pharmaceutical compositions containing them and their use as antibacterial agents.

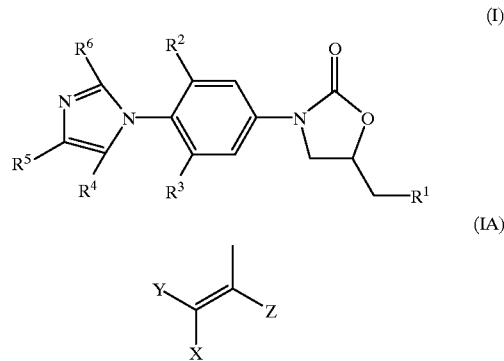

8 Claims, No Drawings

FOREIGN PATENT DOCUMENTS

| | | | |
|---|---|---|---|
| 0693491 | 1/1996 | (EP) | C07D/413/04 |
| 0694543 | 1/1996 | (EP) | C07D/413/04 |
| 0694544 | 1/1996 | (EP) | C07D/413/04 |
| 0738726 | 10/1996 | (EP) | C07D/417/04 |
| 0789026 | 8/1997 | (EP) | C07D/413/14 |
| 2458547 | 1/1981 | (FR) | C07D/263/16 |
| 2500450 | 8/1982 | (FR) | C07D/263/20 |
| 2028306 | 3/1980 | (GB) | C07D/263/16 |
| 2053196 | 2/1981 | (GB) | C07D/307/02 |
| 2054575 | 2/1981 | (GB) | C07D/263/20 |
| 2094299 | 9/1982 | (GB) | C07D/263/20 |
| 2141716 | 1/1985 | (GB) | C07D/263/20 |
| 93/09103 | 5/1993 | (WO) | C07D/263/20 |
| 93/23384 | 11/1993 | (WO) | C07D/263/20 |
| 94/01110 | 1/1994 | (WO) | A61K/31/42 |
| 94/13649 | 6/1994 | (WO) | C07D/263/20 |
| 95/07271 | 3/1995 | (WO) | C07D/263/20 |
| 95/14684 | 6/1995 | (WO) | C07D/263/20 |
| 95/25106 | 9/1995 | (WO) | C07D/413/10 |
| 96/13502 | 5/1996 | (WO) | C07D/413/10 |
| 96/15130 | 5/1996 | (WO) | C07D/491/48 |
| 96/23788 | 8/1996 | (WO) | C07D/413/10 |
| 96/35691 | 11/1996 | (WO) | C07D/487/04 |
| 97/09328 | 3/1997 | (WO) | C07D/413/10 |
| 97/10223 | 3/1997 | (WO) | C07D/263/20 |
| 97/10235 | 3/1997 | (WO) | C07D/307/52 |
| 97/14690 | 4/1997 | (WO) | C07D/307/32 |
| 97/19089 | 5/1997 | (WO) | C07D/498/04 |
| 97/21708 | 6/1997 | (WO) | C07D/413/12 |
| 97/27188 | 7/1997 | (WO) | C07D/413/10 |
| 97/30981 | 8/1997 | (WO) | C07D/263/20 |
| 97/30995 | 8/1997 | (WO) | C07D/413/10 |
| 97/31917 | 9/1997 | (WO) | C07D/413/10 |
| 97/37980 | 10/1997 | (WO) | C07D/263/24 |
| 97/43280 | 11/1997 | (WO) | C07D/405/10 |
| 98/01446 | 1/1998 | (WO) | C07D/413/12 |
| 98/01447 | 1/1998 | (WO) | C07D/413/12 |
| 98/07708 | 2/1998 | (WO) | C07D/261/04 |

OTHER PUBLICATIONS

Barbachyn, M., et al., "Synthesis and Antibacterial Activity of New Tropone–Substituted Phenyloxazolidinone Antibacterial Agents. 1. Identification of Leads and Importance of the Tropone Substitution Pattern.", *Bioorganic and Medicinal Chemistry Lett.*, 6, 1003–1008, (1996).

Barbachyn, M., et al., "Synthesis and Antibacterial Activity of New Tropone–Substituted Phenyloxazolidinone Antibacterial Agents. 2. Modification of the Phenyl Ring—the Potentiating Effect of Fluorine Substitution on In Vivo Activity.", *Bioorganic and Medicinal Chemistry Lett.*, 6, 1009–1014, (1996).

Barry, A., et al., "In Vitro Evaluation of DuP 105 and DuP 721, Two New Oxazolidinone Antimicrobial Agents", *Antimicrobial Agents and Chemotherapy*, 32, 150–152, (1988).

Borthwick, A., et al., "5–(Acetamidomethyl)–3–Aryldihydrofuran–2–ones, and 5–(Acetamidomethyl)–3–Aryltetrahydrofuran–2–ones, Two New Classes of Antibacterial Agents", *Med. Chem. Res.*, 6, 22–27, (1996).

Brickner, S., et al., "Oxazolidinone Antibacterial Agents", *Current Pharmaceutical Design*, 2, 175–194, (1996).

Brickner, S., et al., "Synthesis and Antibacterial Activity of U–100592 and U–100766, Two Oxazolidinone Antibacterial Agents for the Potential Treatment of Multidrug–Resistant Gram–Positive Bacterial Infections", *J. Medical Chemistry*, 39, 673–679, (1996).

Brumfitt, W., et al., "Antibacterial Oxazolidinones: In Vitro Activity of a New Analogue, E3709", *Diagn. Microbiol. Infect. Dis.*, 15, 621–625, (1992).

Brumfitt, W., et al., "In–vitro Microbiological Activities of DuP 105 and DuP 721, Novel Synthetic Oxazolidinones", *J. Antimicrobial Chemotherapy*, 21, 711–720, (1988).

Brumfitt, W., et al., "Variation in Response of Gram–Positive cocci to the Combination DuP 721 and ciprofloxacin", *J. Antimicrob. Chemotherapy*, 24, 465–466, (1989).

Daly, J., et al., "Activity and Mechanism of Action of DuP 105 and DuP 721, New Oxazolidinone Compounds", *J. Antimicrobial Chemotherapy*, 21, 721–730, (1988).

Denis, A., et al., "5–Aryl–beta,gamma Butenolide, A New Class of Antibacterial Derived from the N–Aryl Oxazolidinone DUP 721", *Bioorganic and Medicinal Chemistry Lett.*, 4, 1925–1930, (1994).

Dostert, P., et al., "Structural Modifications in Oxazolidinone Series Leading to Type A or B Selective Monoamine Oxidase Inhibitors", *Int. Congress Series; Excerpta Medica*, 564, 197–208, (1982).

Eliopoulos, G., et al., "In Vitro Activities of New Oxazolidinone Antimicrobial Agents against Enterococci", *Antimicrobial Agents and Chemotherapy*, 40, 1745–1747, (1996).

Eustice, D., et al., "An Automated Pulse Labelling Method for Structure–Activity Relationship Studies with Antibacterial Oxazolidinones", *Drugs Exp. Clin. Res.*, 16, 149–155, (1990).

Eustice, D., et al., "Mechanism of Action of DuP 721: Inhibition of an Early Event during Initiation of Protein Synthesis", *Antimicrobial Agents and Chemotherapy*, 32, 1218–1222, (1988).

Eustice, D., et al., "The Mechanism of Action of DuP 721, a New Antibacterial Agent: Effects on Macromolecular Synthesis", *Biochem. and Biophys. Res. Comm.*, 150, 965–971, (1988).

Ford, C., et al., "In Vivo Activities of U–100592 and U–100766, Novel Oxazolidinone Antimicrobial Agents, against Experimental Bacterial Infections", *Antimicrobial Agents and Chemotherapy*, 40, 1508–1513, (1996).

Grega, K., et al., "Regioselective Metalation of Fluoroanilines. An Application to the Synthesis of Fluorinated Oxazolidinone Antibacterial Agents", *J. Org. Chem.*, 60, 5255–5261, (1995).

Gregory, W., et al., "Antibacterials. Synthesis and Structure–Activity Studies of 3–Aryl–2–oxooxazolidines. 1. The "B" Group", *J. Med. Chem.*, 32, 1673–1681, (1989).

Gregory, W., et al., "Antibacterials. Synthesis and Structure–Activity Studies of 3–Aryl–2–oxooxazolidines. 2. The "A" Group", *J. Med. Chem.*, 33, 2569–2578, (1990).

Hutchinson, D., et al., "Piperazinyl Oxazolidinones: Structure Activity Relationshipd of a New Class of Oxazolidinone Antibacterial Agents", *Abstract: Interscience Congress of Antimicrobial Agents and Chemotherapy*, 8–14, (Sep. 17–20, 1995).

Jones, R., et al., "In Vitro Antimicrobial Activities and Spectra of U–100592 and U–100766, Two Novel Fluorinated Oxazolidinones", *Antimicrobial Agents and Chemotherapy*, 40, 720–726, (1996).

Jorgensen, J., et al., "In Vitro Activities of the Oxazolidinone Antibiotics U–100592 and U–100766 against *Staphylococcus aureus* and Coagulase–Negative Staphylococcus Species", *Antimicrobial Agents and Chemotherapy*, 41, 465–467, (Feb. 1997).

Kaatz, G., et al., "In Vitro Activities of Oxazolidinone Compounds U100592 and U100766 against *Staphylococcus aureus* and *Staphylococcus epidermis*", *Antimicrobial Agents and Chemotherapy*, 40, 799–801, (1996).

Lin, A., et al., "The Oxazolidinone Eperezolid Binds to the 50S Ribosomal Subunit and Competes with Binding of Chloramphenicol and Lincomycin", *Antimicrobial Agents and Chemotherapy*, 41, 2127–2131, (1997).

Lizondo, J., et al., "Linezolid U–100766", *Drugs of the Future*, 21, 1116–1123, (1996).

Lund, J., et al., "Hypersegmented Megakaryocytes and Megakaryocytes with Multiple Separate Nuclei in Dogs Treated with PNU–100592, an Oxazolidinone Antibiotic", *Toxicologic Pathology*, 25, 339–343, (1997).

Maple, P., et al., "Comparative in–vitro activity of vancomycin, teicoplanin, ramoplanin (formerly A16686), paldimycin, DuP 721 and DuP 105 against methicillin and gentamicin resistant *Staphylococcus aureus*", *J. Antimicrobial Chemotherapy*, 23, 517–525, (1989).

Mason, E., et al., "In Vitro Activities of Oxazolidinones U–100592 and U–100766 against Penicillin–Resistant and Cephalosporin–Resistant Strains of *Streptococcus pneumoniae*", *Antimicrobial Agents and Chemotherapy*, 40, 1039–1040, (1996).

Mini, E., et al., "Comparative in Vitro Activity of the New Oxazolidinones DuP 721 and DuP 105 against Staphylococci and Streptococci", *Eur. J. Clin. Microbiol. Infect. Dis.*, 8(3), pp. 256–260, (1989).

Mulazimoglu, L., et al., "In Vitro Activities of Two Novel Oxazolidinones (U100592 and U100766), a New Fluoroquinolone (Trovalfloxacin), and Dalfopristin–Quinupristin against *Staphylococcus aureus* and *Staphylococcus epidermis*", *Antimicrobial Agents and Chemotherapy*, 40, 2428–2430, (1996).

Neu, H., et al., "In Vitro Activities of Two Oxazolidinone Antimicrobial Agents, DuP 721 and DuP 105", *Antimicrobial Agents and Chemotherapy*, 32, 580–583, (1988).

Park, C., et al., "Antibacterials. Synthesis and Structure–Activity Studies of 3–Aryl–2–oxooxazolidines. 4. Multiply–Substituted Aryl Derivatives", *J. Med. Chem.*, 53, 1156–1165, (1992).

Ranaldi, G., et al., "Transport of the Antibacterial Agent Oxazolidin–2–One and Derivatives across Intestinal (Caco–2) and Renal (MDCK) Epithelial Cell Lines", *Antimicrobial Agents and Chemotherapy*, 40, 652–658, (1996).

Schaadt, R., et al., "Serum Inhibitory Titers and Serum Bactericidal Titers for Human Subjects Receiving Multiple Doses of the Antibacterial Oxazolidinones Eperezolid and Linezolid", *Diagn. Microbiol. Infect. Dis.*, 28, 201–204, (1997).

Schaus, S., et al., "Dynamic Kinetic Resolution of Epichlorohydrin via Enantioselective Catalytic Ring Operation with TMSN3. Practical Synthesis of Aryl Oxazolidinone Antibacterial Agents", *Tetrahedron Lett.*, 37, 7937–7940, (1996).

Scholl, J., et al., "Micellar Electrokinetic Chromatography as a Generalized Alternative to High–Performance Liquid Chromatography for Purity Determination of a Class of Investigational Antibacterial Drugs", *J. of Chromatography B*, 695, 147–156, (1997).

Seneci, P., et al., "Synthesis and Antimicrobial Activity of Oxazolidin–2–ones and Related Heterocycles", *J. Chem. Soc. Perkin Trans. 1*, 16, 2345–2351, (1994).

Shinabarger, D., et al., "Mechanism of Action of Oxazolidinones: Effects of Linezolid and Eperezolid on Translation Reactions", *Antimicrobial Agents and Chemotherapy*, 41, 2132–2136, (1997).

Silverman, R., et al., "The Oxazolidinone Antibacterial Agent DuP 105 Does Not Act On Cell Wall Biosynthesis Or On A Beta–Lactamase", *Biochemical and Biophysical Research Comm.*, 195, 1077–1080, (1993).

Slee, A., et al., "Oxazolidinones, a New Class of Synthetic Antibacterial Agents: In Vitro and In Vivo Activities of DuP 105 and DuP 721", *Antimicrobial Agents and Chemotherapy*, 31, 1791–1797, (1987).

Spangler, S., et al., "Activities of RPR 106972 (a New Oral Streptogramin), Cefditoren (a New Oral Cephalosporin), Two New Oxazolidinones (U–100592 and U–100766), and Other Oral and Parenteral Agents against 203 Penicillin–Susceptible and –Resistant Pneumococci", *Antimicrobial Agents and Chemotherapy*, 40, 481–484, (1996).

Takagi, H., et al., "Safety Pharmacology Evaluation of the Oxazolidinone, U–100766", *Society of Toxicologists Annual Meeting*, Abstract No. 564, p. 110, (1996).

Tucker, J.A., et al., "Piperazinyl Oxazolidinone Antibacterial Agents Containing a Pyridine, Diazene, or Triazene Heteroaromatic Ring", *J. Med. Chem*, 41, pp. 3727–2735, (1998).

Wang, C., et al., "Chiral Synthesis of DUP 721, A New Antibacterial Agent", *Tetrahedron*, 45 (5), pp. 1323–1326, (1989).

Worth, S., et al., "Quality Control Guidelines for Amoxicillin, Amoxicillin–Clavulanate, Azithromycin, Piperacillin–Tazobactam, Roxithromycin, Ticarcillin, Ticarcillin–Clavulanate, Trovafloxacin (CP 99,219), U–100592, and U–100766 for Various National Committee . . . ", *Diagn. Microbiol. Infect. Dis.*, 24, 87–91, (1996).

Zurenko, G., et al., "In Vitro Activities of U–100592 and U–100766, Novel Oxazolidinone Antibacterial Agents", *Antimicrobial Agents and Chemotherapy*, 40, 839–845, (1996).

Zurenko, G., et al., "Oxazolidinone antibacterial agents: development of the clinical candidates eperezolid and linezolid", *Exp. Opin. Invest. Drugs*, 6, 151–158, (1997).

OXAZOLIDINONE DERIVATIVES AND THEIR USE AS ANTIBACTERIAL AGENTS

This application is a 371 of PCT/GB98/02477 filed Aug. 18, 1998.

The present invention relates to antibiotic compounds and in particular to antibiotic compounds containing an oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a range of compounds which have good activity against a broad range of Gram-positive pathogens including organisms known to be resistant to most commonly used antibiotics. In comparison with compounds described in the art (Walter A. Gregory et al in J. Med. Chem. 1990, 33,2569–2578 and Chung-Ho Park et al in J. Med. Chem. 1992, 35, 1156–1165) the compounds also possess a favourable toxicological profile.

Accordingly the present invention provides a compound of the formula (I):

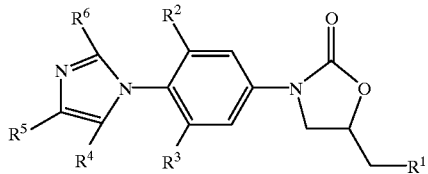

wherein:
$R^1$ is chloro, fluoro, (1–4C)alkanesulfonyloxy, azido, or of the formula —NHC(=O)$R^a$ wherein $R^a$ is hydrogen. (1–4C)alkoxy, chloromethyl, dichloromethyl, cyanomethyl, methoxymethyl, acetylmethyl or (1–4C)alkyl;

$R^2$ and $R^3$ are independently hydrogen or fluoro;

$R^4$ is hydrogen, (1–4C)alkyl, halo or trifluoromethyl;

$R^5$ and $R^6$ are independently selected from hydrogen, (1–4C)alkyl, halo, trifluoromethyl, an acetylene of the formula -≡-H or -≡-(1–4C)alkyl, or a group of the formula (IA)

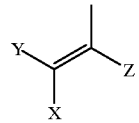

wherein Z is hydrogen or (1–4C)alkyl; X and Y are independently selected from hydrogen, (1–4C)alkyl, halo, cyano, nitro, —S(O)$_n$(1–4C)alkyl (wherein n is 0, 1 or 2), aminosulfonyl, (1–4C)alkylaminosulfonyl, di-(1–4C)alkylaminosulfonyl, trifluoromethyl, pentafluoroethyl, (1–4C)alkanoyl, carbarnoyl, N-(1–4C)alkylcarbamoyl, N,N-di-(1–4C)alkylcarbamoyl; or one of X and Y is selected from the above list and the other is selected from phenyl, phenylcarbonyl, —S(O)$_n$-phenyl (wherein n is 0, 1 or 2), N-(phenyl)carbamoyl, phenylaminosulfonyl, heteroaryl, heteroarylcarbonyl, —S(O)$_n$-heteroaryl (wherein n is 0, 1 or 2), N-(heteroaryl)carbamoyl and heteroarylaminosulfonyl; wherein any phenyl group above may be optionally substituted by up to three substituents independently selected from (1–4C)alkyl, cyano, trifluoromethyl, nitro, halo and (1–4C)alkylsulfonyl; wherein any heteroaryl group in X and Y may be optionally substituted on an available carbon atom by (1–4C)alkyl, and optionally substituted on a suitable nitrogen atom by oxo (to form an N-oxide); provided that X, Y and Z do not define a (2–4C)alkenyl group and provided that at least one of $R^5$ and $R^6$ is a group of the formula (IA) or an acetylene of the formula -≡-H or -≡-(1–4C)alkyl;

or a pharmaceutically acceptable salt thereof.

The term 'alkyl' includes straight chained and branched structures. For example, (1–4C)alkyl includes propyl, isopropyl and t-butyl.

Examples of (1–4C)alkoxy include methoxy, ethoxy, propoxy and tert-butoxy; examples of (1–4C)alkyl include methyl, ethyl, propyl, isopropyl and t-butyl; examples of halo include fluoro, chloro and bromo; examples of (1–4C) alkylS(O)$_n$— include methylthio, ethylthio, methylsulfinyl, ethylsulfinyl, methylsulfonyl and ethylsulfonyl; examples of (1–4C)alkylaminosulfonyl include methylaminosulfonyl and ethylaminosulfonyl; examples of di-(1–4C)alkylaminosulfonyl include dimethylaminosulfonyl and diethylaminosulfonyl; examples of (1–4C)alkanoyl include formyl, acetyl and propionyl; examples of N-(1–4C)alkylcarbamoyl include methylcarbamoyl and ethylcarbamoyl; examples of N,N-di-(1–4C)alkylcarbarnoyl include dimethylcarbamoyl and diethylcarbamoyl; examples of (1–4C)alkylsulfonyl include methylsulfonyl and ethylsulfonyl; examples of —S(O)$_n$-phenyl include phenylthio and phenylsulfonyl; examples of —S(O)$_n$-heteroaryl include pyridylthio, pyridylsulfonyl, pyrazinylthio and pyrazinylsulfonyl; examples of N-(heteroaryl)carbamoyl include pyridylcarbamoyl and pyrazinylcarbamoyl; examples of (2–4C)alkenyl group include vinyl and allyl; examples of an acetylene of the formula -≡-(1–4C)alkyl include 2-methylethynyl and 2-ethylethynyl.

The term heteroaryl refers to pyridyl, pyrimidinyl, pyrazinyl and pyridazinyl linked via any ring carbon atom; and also to 5-membered heteroaryl rings containing no more than two heteroatoms, at least one of which is nitrogen (for example thiazole or imidazole), linked via any ring carbon atom.

Suitable pharmaceutically-acceptable salts include acid addition salts such as methanesulfonate, fumarate, hydrochloride, hydrobromide, citrate, maleate and salts formed with phosphoric and sulfuric acid. There may be more than one anion depending on the number of charged functions and the valency of the anions. The salts of certain compounds, for example those in which the group X or Y contains a heteroaryl group (see, for example, Example 11), may be advantageous because of their improved solubility compared with the parent compound.

However, to facilitate isolation of the salt during preparation, salts which are less soluble in the chosen solvent may be preferred whether pharmaceutically-acceptable or not.

The compounds of the present invention have a chiral centre at the C-5 position of the oxazolidinone ring. The pharmaceutically active enantiomer is of the formula (IB):

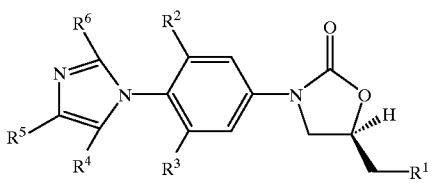

(IB)

The present invention includes the pure enantiomer depicted above or mixtures of the 5(R) and 5(S) enantiomers, for example a racemic mixture. If a mixture of 5(R) and 5(S) is used, a larger amount (depending up on the ratio of the enantiomers) will be required to achieve the same effect as the same weight of the pharmaceutically active enantiomer. For the avoidance of doubt the enantiomer depicted above could be either 5R or 5S depending upon the value of R$^1$. For example, when R$^1$ is acetamido, the enantiomer depicted above is the 5S enantiomer.

It is also to be understood that certain compounds of the formula (I) can exist in solvated as well as unsolvated forms such as, for example, hydrated forms. It is to be understood that the invention encompasses all such solvated forms which possess antibacterial activity.

The compounds of the present invention can exist in the form of Z- and E-isomers when the group R$^5$ is suitably substituted by X Y and Z. The invention includes both the Z- and E-isomers, and mixtures thereof.

In another aspect of the invention there is provided a compound of the formula (I), or a pharmaceutically-acceptable salt thereof, as described in claim 1, but excluding the possibility that at least one of R$^5$ and R$^6$ is an acetylene of the formula -≡-H or -≡-(1–4C)alkyl, and also excluding the option of any heteroaryl group in X and Y being optionally substituted on an available carbon atom by (1–4C)alkyl, and optionally substituted on a suitable nitrogen atom by oxo (to form an N-oxide).

In another aspect of the invention there is provided a compound of the formula (I), or a pharmaceutically-acceptable salt thereof, as described anywhere above wherein the term heteroaryl refers to unsubstituted pyridyl, pyrimidinyl, pyrazinyl and pyridazinyl.

Particularly preferred compounds of the invention comprise a compound of formula (I), or a pharmnaceutically-acceptable salt thereof, wherein R$^1$ to R$^6$ have the values disclosed hereinbefore, or any of the following values:

Preferably R$^1$ is of the formula —NHC(=O)(1–4C)alkyl.
Most preferably R$^1$ is acetamido.
Preferably one of R$^2$ and R$^3$ is hydrogen and the other is fluoro.
In another aspect both R$^2$ and R$^3$ are fluoro.
In a further aspect both R$^2$ and R$^3$ are hydrogen.
Preferably R$^4$ is hydrogen or halo.
Preferably only R$^5$ is a group of the formula (IA).
Preferably R$^4$ is hydrogen and R$^6$ is hydrogen when R$^5$ is a group of the formula (IA).
Preferably Z is hydrogen.
Preferably any heteroaryl group in X or Y is unsubstituted.
Preferably when X or Y contains a heteroaryl group, it is pyridyl (preferably pyrid-2-yl or pyrid-4-yl).
Preferably X and Y are independently selected from halo, cyano, nitro and (1–4C)alkanoyl.
More preferably X and Y are independently selected from halo and cyano.

In another aspect Z is hydrogen, one of X and Y is hydrogen and the other is selected from phenyl, phenylcarbonyl, —S(O)$_n$-phenyl (wherein n is 0, 1 or 2), N-(phenyl)carbamoyl, phenylaminosulfonyl, heteroaryl, heteroarylcarbonyl, —S(O)$_n$-heteroaryl (wherein n is 0, 1 or 2), N-(heteroaryl)carbamoyl and heteroarylaminosulfonyl; wherein any phenyl group above may be optionally substituted by up to three substituents independently selected from (1–4C)alkyl, cyano, trifluoromethyl, nitro, halo and (1–4C)alkylsulfonyl; and wherein any heteroaryl group may be optionally substituted on an available carbon atom by (1–4C)alkyl, and optionally substituted on a suitable nitrogen atom by oxo (to form an N-oxide).

Therefore an especially preferred compound is of the formula (I), wherein R$^1$ is acetamido; one of R$^2$ and R$^2$ is hydrogen and the other is fluoro; R$^4$ and R$^6$ are hydrogen; R$^5$ is a group of the formula (IA) wherein Z is hydrogen and X and Y are independently selected from halo, cyano, nitro and (1–4C)alkanoyl.

A further especially preferred compound is of the formula (I), or a pharnaceutically-acceptable salt thereof, wherein R$^1$ is acetamido; one of R$^2$ and R$^3$ is hydrogen and the other is fluoro; R$^4$ and R$^6$ are hydrogen; R$^5$ is a group of the formula (IA) wherein Z is hydrogen, one of X and Y is hydrogen and the other is selected from halo, cyano, nitro and (1–4C)alkanoyl.

In another aspect of the invention there is provided a compound of the formula (I), or a pharmaceutically-acceptable salt thereof, wherein $R^1$ is acetamido; one of $R^2$ and $R^3$ is hydrogen and the other is fluoro; $R^4$ and $R^6$ are hydrogen; $R^5$ is a group of the formula (IA) wherein Z is hydrogen, one of X and Y is hydrogen and the other is selected from phenyl, phenylcarbonyl, —S(O)$_n$-phenyl (wherein n is 0, 1 or 2), N-(phenyl)carbamoyl, phenylarninosulfonyl, heteroaryl, heteroarylcarbonyl, —S(O)$_n$-heteroaryl (wherein n is 0, 1 or 2), N-(heteroaryl)carbamoyl and heteroarylaminosulfonyl; wherein any phenyl group above may be optionally substituted by up to three substituents independently selected from (1–4C)alkyl, cyano, trifluoromethyl, nitro, halo and (1–4C)alkylsulfony); and wherein any heteroaryl group may be optionally substituted on an available carbon atom by (1–4C)alkyl, and optionally substituted on a suitable nitrogen atom by oxo (to form an N-oxide).

In the above aspect of the invention, those compounds, or a pharmaceutically-acceptable salt thereof, in which one of X and Y is selected from heteroaryl, heteroarylcarbonyl, —S(O)$_n$-heteroaryl (wherein n is 0, 1 or 2), N-(heteroaryl)carbamoyl and heteroarylaminosulfonyl are preferred, especially those in which one of X and Y is heteroaryl.

Particular compounds of the present invention include the following mixtures of E- and Z- isomers, and the individual E- and Z- isomers contained in the mixtures:

N-[(5S)-3-(3-Fluoro-4-(4-(E/Z-2-cyanoethenyl)imidazol-1-yl)phenyl)-2-oxooxazolidin-5-ymethyl]acetamide;

N-[(5S)-3-(3-Fluoro-4-(4-(2,2-dibromoethenyl)imidazol-1-yl)phenyl )-2-oxooxazolidin-5-ylmethyl]acetamide;

N-[(5S)-3-(3-Fluoro-4-(4-(E/Z-2-bromoethenyl)imidazol-1-yl)phenyl)-2-oxooxazolidin-5-ylmethyl]acetamide;

N-[(5S)-3-(3-Fluoro-4-(4-(2,2-dichloroethenyl)imidazol-1-yl)phenyl)-2-oxooxazolidin-5-ylmethyl]acetamide;

N-[(5S)-3-(3-Fluoro-4-(4-(E/Z-2-chloroethenyl)imidazol-1-yl)phenyl)-2-oxo-5-oxazolidinylmethyl]acetamide.

A further particular compound of the present invention is the following compound:

N-[(5S)-3-(3-Fluoro-4-(4-(2,2-difluoroethenyl)imidazol-1-yl)phenyl)-2-oxooxazolidin-5-ylmethyl]acetamnide.

Further particular compounds of the present invention include the following mixtures of E- and Z- isomers, and the individual E- and Z- isomers contained in the mixtures:

N-[(5S)-3-(3,5-Difluoro-4-(4-(E/Z-2-cyanoethenyl)imidazol-1-yl)phenyl)-2-oxooxazolidin-5-ylmethyl]acetamide;

N-[(5S)-3-(3,5-Difluoro-4-(4-(2,2-dibromoethenyl)imidazol-1-yl)phenyl)-2-oxooxazolidin-5-ylmethyl]acetamide;

N-[(5S)-3-(3,5-Difluoro-4-(4-(E/Z-2-bromoethenyl)imidazol- 1-yl)phenyl)-2-oxooxazolidin-5-ylmethyl]acetamide;

N-[(5S)-3-(3,5-Difluoro-4-(4-(2,2-dichloroethenyl)imidazol- 1-yl)phenyl)-2-oxooxazolidin-5-ylmethyl]acetamide;

N-[(5S)-3-(3,5-Difluoro-4-(4-(E/Z-2-chloroethenyl)imidazol- 1-yl)phenyl)-2-oxo-5-oxazolidinylmethyl]acetamide.

Further particular compounds of the present invention include the following mixtures of E- and Z- isomers, and the individual E- and Z- isomers contained in the mixtures:

N-[(5S)-3-(3-Fluoro-4-(4-(E/Z-2-(pyrid-4-yl)ethenyl)imidazol-1-yl)phenyl)-2-oxooxazolidin-5-ylmethyl]acetamide;

N-[(5S)-3-(3-Fluoro-4-(4-(E/Z-2-(1-oxo-pyrid-2-yl)ethenyl)imidazol-1-yl )phenyl)-2-oxooxazolidin-5-ylmethyl]acetamide;

N-[(5S)-3-(3-Fluoro-4-(4-(E/Z-2-(2,4-difluorophenyl)ethenyl)imidazol-1-yl)phenyl)-2-oxooxazolidin-5-ylmethyl]acetamide;

N-[(5S)-3-(3-Fluoro-4-(4-(E/Z-2-(pyrid-2-yl)ethenyl)imidazol-1-yl)phenyl)-2-oxooxazolidin-5-ylmethyl]acetamide; N-[(5S)-3-(3-Fluoro-4-(4-(E/Z-2-(4-methoxyphenyl )ethenyl)imidazol-1-yl)phenyl)-2-oxooxazolidin-5-ylmethyl]acetamide, or a pharmnaceutically-acceptable salt of a compound containing a pyridyl group with an unsubstituted nitrogen atom.

An especially preferred compound of the present invention is the following compound: N-[(5S)-3-(3-Fluoro-4-(4-(E-2-(pyrid-2-yl)ethenyl)imidazol-1-yl)phenyl)-2-oxooxazolidin-5-ylmethyl]acetamide, or a pharmaceutically acceptable salt thereof A further particular compound of the present invention is the following compound:

N-[(5S)-3-(3-Fluoro-4-(4-ethynylimidazol-1-yl)phenyl)-2-oxooxazolidin-5-ylmethyl]acetamide.

In a further aspect the present invention provides a process for preparing a compound of the formula (I) or a pharmaceutically acceptable salt thereof. The compounds of the formula (I) may be prepared by deprotecting a compound of the formula (II):

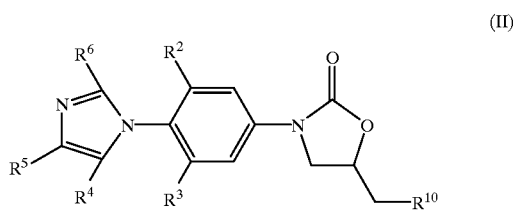

(II)

wherein $R^2$ to $R^6$ are as hereinabove defined and $R^{10}$ is $R^1$ or protected $R^1$, and thereafter if necessary forming a pharmaceutically acceptable salt.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

Examples of protecting groups for amide groups include aralkoxymethyl (eg. benzyloxymethyl and substituted benzyloxymethyl); alkoxymethyl (eg. methoxymethyl and trimethylsilylethoxymethyl); tri alkyl/arylsilyl (eg. trimethylsilyl, t-butyldimethylsily, t-butyldiphenylsilyl); tri alkyl/arylsilyloxymethyl (eg. t-butyldimethylsilyloxymethyl, t-butyldiphenylsilyloxymethyl); 4-alkoxyphenyl (eg. 4-methoxyphenyl); 2,4-di(alkoxy)phenyl (eg. 2,4-dimethoxyphenyl); 4-alkoxybenzyl (eg. 4-methoxybenzyl);

2,4-di(alkoxy)benzyl (eg. 2,4-di(methoxy)benzyl); alk-1-enyl (eg. allyl, but-1-enyl and substituted vinyl eg. 2-phenylvinyl); allyloxycarbonyl; and (1–4C)alkoxycarbonyl or benzyloxycarbonyl.

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Alk-1-enyl groups may be introduced by reacting the amide with the appropriate aldehyde and removed with acid. Allyloxycarbonyl, (1–4C)alkoxycarbonyl and benzyloxycarbonyl groups may be introduced using standard techniques and removed for example, by reacting with acid for (1–4C)alkoxycarbonyl; by hydrogenation for benzyloxycarbonyl; and by reaction using Pd(0) for allyloxycarbonyl.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II) and pharmaceutically acceptable salts thereof can be prepared by the following processes (a) to (j). Certain novel intermediates, for example compounds of the formula (I) or (II) wherein $R^1$ or $R^{10}$ is hydroxy and amino, and processes for their preparation, are provided as a further feature of the invention.

(a) by modifying a substituent in or introducing a substituent into another compound of the formula (I) or (II);

(b) when $R^1$ or $R^{10}$ is azido, by reacting a compound of the formula (III) with a source of azide:

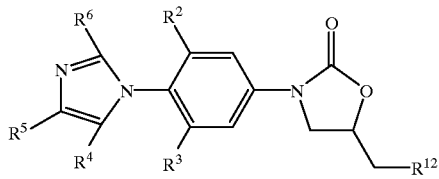

(III)

(c) when $R^1$ or $R^{10}$ is of the formula —NHC(=O)$R^a$, by introducing —C(=O)$R^a$ into a compound of the formula (I) or (II) wherein $R^1$ or $R^{10}$ is amino; a compound in which $R^1$ or $R^{10}$ is amino, may be obtained by reducing a compound of the formula (I) or (II) wherein $R^1$ or $R^{10}$ is azido;

(d) when $R^1$ or $R^{10}$ is chloro, fluoro, (1–4C)alkanesulfonyloxy or (1–4C)alkylaminocarbonyloxy, from a compound of the formula (I) or (II) wherein $R^1$ or $R^{10}$ is hydroxy; a compound in which $R^1$ or $R^{10}$ is hydroxy, may be obtained by reacting a compound of the formula (V) with a compound of the formula (VI):

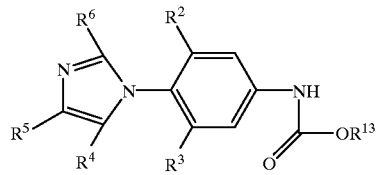

(V)

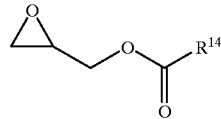

(VI)

(e) when $R^1$ or $R^{10}$ is chloro from a compound of the formula (III);

(f) when $R^5$ and/or $R^6$ is a group of the formula (IA),

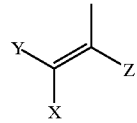

(IA)

by Wittig, or other related ylide chemistry, such as the reaction in the presence of a base between a compound of the formula (I) or (II) wherein $R^5$ and/or $R^6$ is a —C(Z)O group and a phosphonium salt of the formula (X)(Y)CH—$P^+R^{15}R^{16}R^{17}Q^-$ or a phosphonate of the formula (X)(Y)CH—P(O)$R^{16}R^{17}$;

(g) when $R^5$ and/or $R^6$ is a group of the formula (IA), by the base or acid condensation of a compound of the formula (I) or (II) wherein $R^5$ and/or $R^6$ is a —C(Z)O group and a compound of the formula X—$CH_2$—Y (see for example, the acid condensation in Example 14, where X is pyrid-4-yl and Y is hydrogen);

(h) when $R^{10}$ is of the formula —N($CO_2$ $R^{18}$)CO(1–4C)alkyl; from a compound of the formula (I) and (II) wherein $R^1$ or $R^{10}$ is hydroxy;

(i) when one of $R^5$ and $R^6$ is an acetylene of the formula —≡-H or —≡-(1–4C)alkyl; from a compound of the formula (I) and (II) wherein one of $R^1$ and $R^6$ is of the formula (IA) wherein Z is hydrogen and one of X and Y is halo and the other is hydrogen or (1–4C)alkyl;

(j) when a suitable N-oxide of a heteroaryl group in $R^5$ or $R^6$ is required, by preparation directly from a corresponding parent compound of the formula (I); wherein $R^2$ to $R^6$, $R^{10}$ and Z are as hereinabove defined, $R^{12}$ is mesyloxy or tosyloxy, $R^{13}$ is (1–6C)alkyl or benzyl, $R^{14}$ is (1–6C)alkyl, $R^{15}$–$R^{17}$ are independently selected from (1–4C)alkyl, allyl, phenyl, benzyl, (1–6C)alkoxy, phenoxy and di-(1–6C)alkylamino; or any two of $R^{15}$–$R^{17}$ represent o-phenylenedioxy and the third is selected from the above values for $R^{15}$–$R^{17}$; or one of $R^{15}$–$R^{17}$ is (1–4C)alkyl. allyl, benzyl or phenyl, and the other two values are independently selected from (1–4C)alkyl and phenyl; wherein any phenyl group is optionally substituted with up to three substituents independently selected from (1–3C)alkyl and (1–3C)alkoxy; Q is an anion such as chloride, bromide or iodide; $R^{18}$ is (1–4C)alkyl, benzyl or allyl; and thereafter if necessary:

i) removing any protecting groups;
ii) forming a pharmaceutically acceptable salt, or N-oxide of a heteroaryl group in $R^5$ or $R^6$.

Methods for converting substituents into other substituents are known in the art. For example an alkylthio group may be oxidised to an alkylsulfinyl or alkysulfonyl group, a bromo group converted to an alkylthio group or a bromo group to a cyano group.

A compound of the formula (I) or (II) wherein $R^1$ or $R^{10}$ is azido may be prepared, for example, by reacting a compound of the formula (III) with sodium azide in an inert solvent such as DMF in a temperature range of ambient to 100° C., normally in the region of 75° C.–85° C. A compound of the formula (III) may be prepared by converting the hydroxy group in a compound of the formula (I) or (II) wherein $R^1$ or $R^{10}$ is hydroxy into a tosyloxy or mesyloxy group by standard methods known in the art. For example, by reacting the compound of the formula (III) with tosyl chloride or mesyl chloride in the presence of a mild base such as triethylamine, or pyridine.

When $R^a$ is (1l–4C)alkyl, the group —C(=O)(1–4C)alkyl may be introduced into a compound of the formula (I) or (II) wherein $R^1$ or $R^{10}$ is amino by standard acetylation procedures. For example, the amino group may be acetylated to give an acetamido group using the Schotten-Baumrann procedure i.e. reacting the compound of the formula (I) or (II) wherein $R^1$ or $R^{10}$ is amino with acetic anhydride in aqueous sodium hydroxide and THF in a temperature range of 0° C. to 60° C., preferably between 0° C. and ambient temperature. The acylation may be carried out in situ following the catalytic hydrogenation of a compound of the formula (I) or (II) wherein $R^1$ or $R^{10}$ is azido, by performing the hydrogenation in the presence of acetic anhydride.

When $R^a$ is hydrogen, the —CHO group may be introduced into the compound of the formula (I) or (II) wherein $R^1$ or $R^{10}$ is amino (amino compound) by reacting the latter compound in formic acetic anhydride, in an inert organic solvent such as THF, in a temperature range of 0° C. to ambient temperature, or by reacting it with ethyl formate in an inert organic solvent in the temperature range of 50–100° C.

When $R^a$ is (1–4C)alkoxy, the —COO(1–4C)alkyl group may be introduced into the amino compound by reacting the latter compound with (1–4C)alkyl chloroformate. in the presence of an organic base such as triethylamine, in an organic solvent such as dichloromethane and in a temperature range of 0° C. to ambient temperature.

When $R^a$ is chloromethyl, dichloromethyl, cyanomethyl or methoxymethyl, the —C(=O)$R^a$ group may be introduced into the amino compound by reacting the latter compound with the appropriate acid chloride under standard conditions. The acid chloride may be prepared from the appropriate acid. When $R^a$ is acetylmethyl, the —C(=O)$R^a$ group may be introduced into the amino compound by reacting the latter compound with diketene, in an inert organic solvent such as THF, in a temperature range of 0° C. to ambient temperature.

Alternatively, the amino compound may be reacted with the appropriate acid anhydride, in dichloromethane or THF, in the presence of an organic base such as triethylamine and in a temperature range of 0° C. to ambient temperature, or the amino compound may be reacted with the appropriate acid in the presence of 1-(3-dimethylaminopropyl)-3-ethylcarbodiimide hydrochloride and an organic base such as triethylamine, in an organic solvent such as dichloromethane, in a temperature range of 0° C. to ambient temperature.

Suitable reducing agents for reducing azido to amino in a compound of the formula (I) or (II) include trietbylamine/hydrogen sulfide, triphenylphosphine or phosphite ester, or hydrogen in the presence of a catalyst. More specifically the reduction of the azido group may be carried out by heating it in an aprotic solvent, such as 1,2-dimethoxyethane, in the presence of P(OMe)$_3$ and subsequently heating in 6N aqueous hydrochloric acid, or reacting it with hydrogen in the presence of palladium on carbon in a suitable solvent such as DMF, ethyl acetate or ethanol. For further details on the reduction of azides to amines see U.S. Pat. No. 4,705,799. The azido compound may be reduced and converted to a compound of the formula (I) or (II), wherein $R^1$ or $R^{10}$ is acetamido, in situ using acetic anhydride in an aprotic solevent such as DMF.

A compound of the formula (I) or (II) wherein $R^1$ or $R^{10}$ is fluoro may be prepared by reacting a compound of the formula (I) or (II) wherein $R^1$ or $R^{10}$ is hydroxy (hydroxy compound) with a fluorinating agent such as diethylaminosulfur trifluoride in an organic solvent such as dichloromethane in the temperature range of 0° C. to ambient temperature.

When $R^1$ or $R^{10}$ is chloro, the compound of the formula (I) or (II) may be formed by reacting the hydroxy compound with a chlorinating agent. For example, by reacting the hydroxy compound with sulfinyl chloride in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature.

The (1–4C)alkanesulfonyloxy compound may be prepared by reacting the hydroxy compound with (1–4C)alkanesulfonyl chloride in the presence of a mild base such as triethylamine or pyridine.

A compound of the formula (I) or (II) wherein $R^1$ or $R^{10}$ is chloro may also be prepared from a compound of the formula (III), by reacting the latter compound with lithium chloride and crown ether, in a suitable organic solvent such as THF, in a temperature range of ambient temperature to reflux. A compound of the formula (I) or (II) wherein $R^1$ or $R^{10}$ is (1–4C)alkylthio or (1–4C)alkoxy may be prepared by reacting the compound of the formula (III) with sodium thio(1–4C)alkoxide or sodium (1–4C)alkoxide respectively, in an alcohol or THF, in a temperature range of 0° C. to reflux.

Compounds of the formulae (V) and (VI) are conveniently reacted together in the presence of a strong base such as butyl lithium, lithium bistrimethylsilylamide, sodium hydride, lithium diisopropylamide or lithium tert-butoxide. The reaction is conveniently carried out in an inert solvent such as THF, DMF, N,N$^1$-dimethylpropyleneurea (DMPU) or N-methylpyrrolidone in a temperature range of −78° C. to −50° C. for the deprotonation and cyclisation. Suitable values for $R^{13}$ include ethyl and benzyl and suitable values for $R^{14}$ include ethyl and n-propyl, preferably n-propyl.

A compound of the formula (V) is conveniently prepared by reacting a chloroforrnate of the formula ClCOOR$^{13}$ with a compound of the formula (VA):

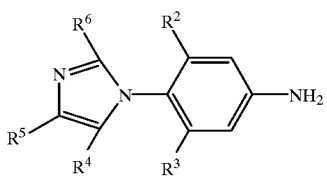

(VA)

wherein $R^2$ to $R^6$ are as hereinabove defined. The reaction is conveniently carried out in the presence of an inorganic or organic base such as sodium bicarbonate or an amine base such as dimethylaniline, the former in a solvent such as acetone/water and the latter in an organic solvent such as THF, toluene, DMF or acetonitrile.

A compound of the formula (VA) may be prepared by reducing a compound of the formula (VB):

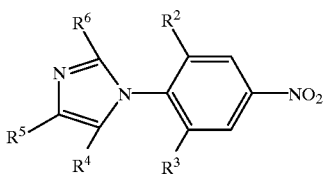

(VB)

wherein $R^2$ to $R^6$ are as hereinabove defined.

Many reduction methods suitable for the reduction of a nitro to an amino group are known in the art, for example catalytic hydrogenation, metal reductions or with reducing agents such as sodium hydrosulfite. Suitable catalysts in catalytic hydrogenation include Raney nickel, platinum metal and its oxide, rhodium, palladium-on-charcoal and Wilkinson's catalyst $RhCl(Ph_3P)_3$. Catalyst hydrogenation is conveniently carried out in the temperature range 0° C.–150° C., but preferably at ambient temperature at slightly above atmospheric pressure.

A compound of the formula (VB) is conveniently prepared by reacting together compounds of the formulae (VII) and (VC):

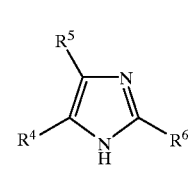

(VII)

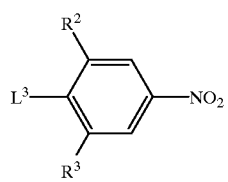

(VC)

wherein $R^2$, $R^3$ and $R^7$–$R^9$ are as hereinabove defined and $L^3$ is a leaving group, preferably halo and in particular fluoro.

The reaction between compounds of the formulae (VII) and (VC) is carried out in the presence of an organic or inorganic base such as sodium bicarbonate, potassium carbonate or an amine base such as diisopropylethylamine, in an inert solvent such as acetonitrile, DMF, DMPU or N-methylpyrrolidone, in a temperature range of 50° C.–150° C.

Compounds of the formula (VII) may be prepared by introducing substituents into or modifying substituents in a known optionally substituted imidazole ring. Such conversions are well known to the skilled chemist, for example a cyano group may be hydrolysed to a carboxy group which in turn may be reduced to a hydroxymethyl group.

Alternatively compounds of the formula (VII) may be prepared using the methods described in Houben-Weyl, Methoden der organischen Chemie, Heterarene III Teil 3, ed E Schaumann (1994), or The Chemistry of Heterocyclic Compounds, Vol 6, Part 1 "Imidazole and its Derivatives" (1953).

The reaction using Wittig chemistry between a compound of the formula (I) or (II) wherein $R^5$ and/or $R^6$ is a —C(Z)O group and a phosphonium salt of the formula (X)(Y)CH—$P^+R^{15}R^{16}R^{17}Q^-$ or a phosphonate of the formula (X)(Y)CH—$P(O)R^{16}R^{17}$ is conveniently performed in an organic solvent such as toluene, xylene, dichloromethane, tetrahydrofuran, acetonitrile or dimethylformamide. The reaction is carried out in the presence of a base and at a temperature in the range, for example, 20–80° C., preferably at or near ambient temperature. The phosphonium salt or phosphonate is treated with an organic base such as butyl lithium, lithium bistrimethylsilylamide, sodium hydride, lithium diisopropylamide, lithium t-butoxide, or an inorganic base such as potassium carbonate or sodium hydroxide. The skilled chemist will be able to select a suitable base based on the phosphonium salt or phosphonate being used. In certain cases the phosphoranylidene compound formed when a phosphonium salt is treated with a base is sufficiently stable to be used as a reagent (as is illustrated in Example 1) In other cases the desired phosphoranylidene compound is formed in-situ. Certain phosphoranylidene compounds may also be formed by other reactions, such as the reaction between carbon tetrabromide and triphenylphosphine to give $Ph_3P$=$CBr_2$ or between: $CF_2$ carbene (from $ICF_2COO^-$) trapped with triphenylphosphine to give $Ph_3P$=$CF_2$.

A compound of the formula (I) or (II) wherein $R^5$ and/or $R^6$ is a carboxyaldehyde (—CHO) group is conveniently prepared from a compound of the formula (I) or (II) wherein $R^5$ and/or $R^6$ is hydroxymethyl (as illustrated in Example 1). Alkyl analogues (—C(Z)O wherein Z is (1–4C)alkyl) may be made by oxidation of the corresponding hydroxyalkyl group. The skilled chemist will be aware how to prepare such hydroxyalkyl compounds, and the phosphonium salts and phosphonates described above may also be prepared by techniques known to the skilled chemist.

The skilled man will also be aware that alternatives to the above-mentioned Wittig chemistry are possible. For example, suitable As, Sb and Te compounds and also certain Mo, W and Ta compounds may be used in place of the phosphonium salts and phosphonates described above. Also, suitable S, Si, B, Bi and Sn compounds may be used in place of the phosphonates described above. The skilled man will be aware of suitable reaction conditions for such alternative chemistry.

The base condensation of a compound of the formula (I) or (II) wherein $R^5$ and/or $R^6$ is a —C(Z)O group and a compound of the formula X—$CH_2$—Y (which may produce the desired (X)(Y)C=C(Z)— via a group (X)(Y)CH—C(Z)(OH)—) may be performed with a wide variety of bases (weak and strong, inorganic or organic) depending on the acidity of the protons in the X—$CH_2$—Y compound, and in various solvents (hydroxylic and aprotic), depending on their compatibility with the chosen base. The reaction is carried out at a temperature in the range, for example, 20–80° C., preferably at or near ambient temperature. The acid condensation may be performed under the conditions of Example 14 or conditions similar to these. When a group of the formula (X)(Y)CH—C(Z)(OH)— is formed, this may be converted to the desired (X)(Y)C=C(Z)— group via elimination of the elements of water, or via introduction of a leaving group (such as mesylate) followed by elimination (to produce the double bond) in the presence of a mild base.

A compound of the formula (II) wherein $R^{10}$ is of the formula —N($CO_2R^{18}$)CO(1–4C)alkyl is conveniently prepared by reacting a compound of the formula (I) and (II) wherein $R^1$ or $R^{10}$ is hydroxy with an amide of the formula HN($CO_2R^{18}$)CO(1–4C)alkyl under Mitsunobu conditions. For example, in the presence of tri-n-butylphosphine and 1,1'-(azodicarbonyl)dipiperidine in an organic solvent such as THF, and in the temperature range 0° C.–60° C., but preferably at ambient temperature. Details of analogous Mitsunobu reactions are contained in Tsunoda et al, Tet. Letts., 34 1639, (1993). Amides of the formula HN($CO_2R^{18}$)CO(1–4C)alkyl may be prepared by standard procedures of organic chemistry which are within the ordinary skill of an organic chemist.

The formation of a compound of formula (I) or (II) wherein one of $R^1$ and $R^6$ is an acetylene of the formula -≡-H or -≡-(1–4C)alkyl from a compound of the formula (I) and (II) wherein one of $R^5$ and $R^6$ is of the formula (IA) wherein Z is hydrogen and one of X and Y is halo and the other is hydrogen or (1–4C)alkyl may be performed as described, for example, in Example 13, or may be prepared directly from the starting halo-vinyl compound in the presence of a base (such as potassium t-butoxide) in an inert solvent (such as THF), at, or around ambient temperature.

N-oxides of a heteroaryl group in $R^5$ or $R^6$ may be prepared directly from a corresponding parent compound of the formula (I) using techniques well known to the ordinary skilled organic chemist. such as, for example, using a peracid (such as m-chloroperbenzoic acid) or perphthalic acid in a suitable solvent (such as dioxan or a mixture of water and THF) at a suitable temperature (such as ambient temperature).

When an optically active form of a compound of the formula (I) is required, it may be obtained, by carrying out one of the above procedures using an optically active starting material or by resolution of a racemic form of the compound or intermediate using a standard procedure. When a particular geometric (E- or Z-) isomer of a group of the formula (IA) in a compound of the formula (I) is required it may be obtained by separation from a mixture of E- and Z-isomers; or from an intermediate containing the desired E- or Z-isomeric form; or by direct synthesis according to process (f) or (g) above using standard techniques to give the desired isomer.

According to a further feature of the invention there is provided a compound of the formula (I), or a pharmaceutically-acceptable salt thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides the use of a compound of the present invention, or a pharrnaceutically-acceptable salt thereof, for use as a medicament; and the use of a compound of the present invention, or a pharmaceutically-acceptable salt thereof, in the manufacture of a novel medicament for use in the production of an antibacterial effect in a warm blooded animal, such as man.

In order to use a compound of the formula (I) or a pharrnaceutically-acceptable salt thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically-acceptable salt thereof, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness. Compounds of this invention may also contain or be co-administered with bactericidal/permeability-increasing protein product (BPI) or efflux pump inhibitors to improve activity against gram negative bacteria and bacteria resistant to antimicrobial agents.

A suitable phannaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg$^{-1}$ to 20 mgkg$^{-1}$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically acceptable compounds of the present invention are useful antibacterial agents having a good spectrum of activity in vitro against standard Gram-positive organisms, which are used to screen for activity against pathogenic bacteria. Notably, the pharmaceutically acceptable compounds of the present invention show activity against enterococci, pneumococci and methicillin resistant strains of S. aureus and coagulase negative staphylococci. The antibacterial spectrum and potency of a particular compound may be determined in a standard test system.

The antibacterial properties of the compounds of the invention may also be demonstrated in vivo in conventional tests.

The following results were obtained on a standard in vitro test system. The activity is described in terms of the minimum inhibitory concentration (MIC) determined by the agar-dilution technique with an inoculum size of $10^4$ CFU/spot.

The organisms were tested on a standard semi-defined susceptability test medium (IsoSensitest agar), using an inoculum of $10^4$ CFU/spot and an incubation temperature of 37° C. for 24 hours. Typically, compounds are active in the range 0.01 to 128 µg/ml.

The following data were obtained for Example 2:

| ORGANISM | TYPE | MIC (µg/ml) |
| --- | --- | --- |
| Staphylococcus aureus | Oxford | 0.125 |
| Staphylococcus aureus | Novb. Res. | 0.25 |
| Staphylococcus aureus | MRQR | 1.00 |
| Coagulase Negative Staphylococci | MS | 0.06 |
| Coagulase Negative Staphylococci | MR | 0.25 |
| Streptococcus pyogenes | C203 | 0.125 |
| Enterococcus faecalis | — | 0.25 |
| Bacillus subtilis | — | 0.25 |

Novb. Res. = Novobiocin resistant
MRQR = methicillin resistant quinolone resistant
MR = methicillin resistant
MS = methicillin sensitive.

The invention is now illustrated by the following Exarnples in which unless otherwise stated:

(i) evaporations were carried out by rotary evaporation in vacuo and work-up procedures were carried out after removal of residual solids by filtration;

(ii) operations were carried out at ambient temperature, that is typically in the range 18–26° (temperatures are in degrees Celsius ° C.) and in air unless otherwise stated, or unless the skilled person would otherwise work under an inert atmosphere;

(iii) column chromatography (by the flash procedure) was performed on Merck Kieselgel silica (Art. 9385) unless otherwise stated;

(iv) yields are given for illustration only and are not necessarily the maximum attainable;

(v) the structures of the end-products of the formula (I) were confirmed by NMR and mass spectral techniques [proton magnetic resonance spectra were determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus; br, broad; s, singlet; d, doublet; dd, doublet of doublets; t, triplet. m, multiplet; (fast-atom bombardment (FAB)) mass spectral data were obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:

| | |
| --- | --- |
| MPLC | is medium pressure chromatography |
| TLC | is thin layer chromatography |
| DMSO | is dimethylsulfoxide |
| CDCl$_3$ | is deuterated chloroform |
| MS | is mass spectroscopy |
| ESP | is electrospray |
| CI | is chemical ionization |
| DMF | is N,N-dimethylformamide |
| EtOAc | is ethyl acetate |
| THF | is tetrahydrofuran |
| ® | is a Trademark |

EXAMPLE 1

N-[(5S)-3-(3-Fluoro-4-(4-(E/Z-2-cyanoethenyl) imidazol-1-yl)phenyl)-2-oxooxazolidin-5-ylmethyl] acetamide N-[(5S)-3-(3-Fluoro-4-(4-carboxyaldehydeimidazol-1-yl)phenyl)-2-oxooxazolidin-5-ylmethyl]acetamide (173 mg, 0.5 mM) and triphenylphosphoranylideneacetonitrile (301 mg, 1 mM) were dissolved in acetonitrile (10 ml) and heated to 80° C. with stirring under argon for 16 hours. Solvent was evaporated, the residue dissolved in dichloromethane and chromatographed on a 10 g silica Mega Bond Elut® column, eluting with a gradient increasing in polarity from 0 to 10% methanol in dichloromethane. Relevant fractions were combined and evaporated to give the title product (164 mg) as a 1:1 mixture of E and Z isomers.

MS (ESP): 370 (MH$^+$) for $C_{18}H_{16}FN_5O_3$; NMR (DMSO-D6) δ: 1.82 (s, 3H); 3.41 (t, 2H); 3.77 (t, 1H); 4.16 (t, 1H); 4.75 (m, 1H); 5.59 (d, 0.5H, J=11.8 Hz); 6.14 (d, 0.5H, J=17.4 Hz); 7.23 (d, 0.5H, J=11.8 Hz); 7.46 (dm, 1H); 7.51 (d, 0.5H, J=17.4 Hz); 7.68 (t, 1H); 7.76 (dm, 1H); 7.90 (s, 0.5H); 7.97 (s, 0.5H); 8.13 (s, 0.5H); 8.18 (s, 0.5H); 8.22 (t, 1H).

The intermediate for this compound was prepared as follows.

3-Fluoro-4-(4-hydroxvmethylimidazol-1-yl)nitrobenzene 3,4-Difluoronitrobenzene (23.85 g) was dissolved in acetonitrile (180 ml), followed by 4-hydroxymethylimidazole (14.7 g) and ethyldiisopropylamine (65.2 ml). The mixture was stirred and heated to reflux for 2 days. After cooling, acetonitrile was evaporated and the residue was shaken with a mixture of methyl t-butyl ether (200 ml) and water (100 ml), and the solid filtered. After washing with a mixture of methyl t-butyl ether (50 ml) and water (25 ml), the solid was dried in vacuo at 60° C. overnight, to give product (26.8 g) mp 157–159° C.

MS (CI): 237 (MH$^+$) for $C_{10}H_8FN_3O_3$; NMR (DMSO-D6) δ: 4.57 (d, 2H); 5.18 (t, 1H); 7.66 (t, 1H), 8.11 (t, 1H); 8.28 (t, 1H); 8.35 (dm, 1H); 8.54 (dd, 1H).

3-Fluoro-4-(4-t-butyldimethylsilytoxymethylimidazol-1-yl) nitrobernzene

3-Fluoro-4-(4-hydroxymethylimidazol-1-yl)nitrobenzene (26.7 g) and imidazole (15.3 g) were suspended in dry N,N-dimethylformamide (190 ml) and stirred under argon on an ice-bath, t-Butyldimethylsilylchloride (25.5 g) was added in one portion, and stirring continued at ice temperature for 30 minutes, then at ambient temperature overnight. Solvent was evaporated in vacuo at 30° C., the residue diluted with water (200 ml) and extracted into ethyl acetate (700 ml). After washing with water (2×300 ml), brine, and drying over magnesium sulfate, solvent was evaporated (finally on high vacuum) to give an oil which solidified (39.2 g). This was used in the next stage with no further purification.

NMR (DMSO-D6) δ: 0.00 (s, 6H); 0.82 (s, 9H); 4.55 (s, 2H); 7.44 (m, 1H); 7.89 (t, 1H); 8.06 (t, 1H); 8.14 (dm, 1H); 8.33 (dd, 1H).

1-Amino-4-(4-t-butyldimethylsilyloxymeth limidazol-1-yl) fluorobenzene

3-Fluoro-4-(4-t-butyldimethylsilyloxymethylimidazol-1-yl)nitrobenzene (39.0 g) was dissolved in a mixture of methanol (220 ml) and THF (890 ml) and stirred under argon in an ice-bath. Ammonium formate (35.2 g) was added, followed by 10% palladium on charcoal (1.6 g), and the mixture allowed to warm to ambient temperature. Stirring was continued for 2 days. TLC showed a trace of remaining starting material, so further palladium catalyst (0.5 g) was added, and more ammonium formate (35 g) in portions over 6 hours, before leaving to stir overnight, giving essentially one spot as product. The catalyst was filtered off on celite, the cake washed well with methanol/THF, and filtrates evaporated to dryness. The residue was partitioned between ethyl acetate (700 ml) and water (200 ml), the organic layers washed with water, brine, and dried over magnesium sulfate. Evaporation gave an oil (36 g), used in the next stage with no further purification.

MS (ES): 237 (MH$^+$) for $C_{16}H_{24}FN_3OSi$; NMR (DMSO-D6) δ: 0.04 (s, 6H); 0.85 (s, 9H); 4.56 (s, 2H); 5.63 (s, 2H); 6.45 (dd, 1H); 6.48 (dd, 1H); 7.12 (t, 1H); 7.13 (s, 1H); 7.69 (s, 1H).

1-Benzyloxvcarbonylamino-4-(4-t-butyldimethylsilyloxymethylimidazol-1-yl)fluorobenzene 1-Amino-4-(4-t-butyldimethylsilyloxymethylimidazol-1-yl)fluorobenzene (36.1 g) was dissolved in dry dichloromethane (450 ml), treated with pyridine (11.3 ml), then stirred under argon while cooling to −20° C. Benzyl chloroformate (17.7 ml) in dichloromethane (50 ml) was added dropwise, maintaining the temperature. The mixture was then allowed to warm to ambient temperature over 1 hour, then stirred for a further 1.5 hours. The mixture was diluted with aqueous sodium bicarbonate (250 ml), and the organic layer separated. A further extraction with dichloromethane (200 ml) was made, the combined organic layers dried over magnesium sulfate, and solvent evaporated. The resulting oil was re-evaporated with toluene, and purified by chromatography on silica (500 g) in a sinter column, eluting with a gradient from $CH_2Cl_2$ to 50% EtOAc in $CH_2Cl_2$. Evaporation, then re-evaporation with toluene gave solid product (51 g).

MS (ES): 456 (MH$^+$) for $C_{24}H_{30}FN_3O_3Si$; NMR (DMSO-D6) δ: 0.00 (s, 6H); 0.77 (s, 9H): 4.53 (s, 2H); 5.11 (s, 2H); 7.24–7.40 (complex, 7H); 7.46 (t, 1H); 7.53 (dd, 1H); 7.79 (s, 1H); 10.10 (s, 1H).

(5R)-3-(4-(4-t-Butyldimethylsilyloxymethylimidazol-1-yl)-3-fluorophenyl)-5-hydroxy-methyloxazolidin-2-one t-Butanol (6.1 g) in dry THF (50 ml) was stirred under argon at −10°. n-Butyllithium in isohexane (1.6M, 41.3 ml) was added dropwise, the mixture stirred for 10 minutes, then cooled to −70°. A solution of 1-benzyloxycarbonylamino-4-(4-t-butyldimethylsilyloxymethylimidazol-1-yl) fluorobenzene (25.0 g) in dry THF (150 ml) was added dropwise over 20 minutes, then stirred for 20 minutes at −70° C. (R)glycidylbutyrate (9.5 g) in THF (10 ml) was added dropwise over 10 minutes, keeping the temperature below −60° C. Stirring was continued overnight, allowing the temperature to rise to ambient. Saturated sodium bicarbonate solution (200 ml) was added, and the mixture extracted with ethyl acetate (500 and 200 ml). After drying over magnesium sulfate and evaporation the residue was purified by chromatography on silica, eluting with a gradient from dichloromethane to 20% MeOH in dichlorometbane. Relevant fractions were combined and evaporated to give a gum (20.5 g).

MS (ES): 422 (MH$^+$) for $C_{20}H_{28}FN_3O_4Si$; NMR (DMSO-D6) δ: 0.02 (s, 6H); 0.81 (s, 9H); 3.49 (brd, 1H); 3.63 (brd, 1H); 3.80 (dd, 1H); 4.06 (t, 1H); 4.55 (s, 2H); 4.68 (s, 1H); 5.14 (brs, 1H); 7.30 (s, 1H); 7.41 (dm, 1H); 7.58 (t, 1H); 7.68 (dd, 1H); 7.85 (t, 1H).

(5R)-3-(4-(4-t-Butyldimethylsilyloxymethylimidazol-1-yl)-3-fluorophenyl)-5-methane-sulfonyloxymethyloxazolidin-2-one (5R)-3-(4-(4-t-Butyldimethylsilyloxymethylimidazol-1-yl)-3-fluoro-phenyl)-5-hydroxy-methyloxazolidin-2-one (8.0 g) was dissolved in dry dichloromethane (60 ml) with stirring under argon in an ice-bath. Triethylamine (3.44 ml) was added, followed by dropwise addition of methanesulfonyl chloride (1.62 ml). Stirring was continued for 2 hours as the mixture warmed to ambient temperature. Aqueous sodium bicarbonate was added, the organic layer separated, and further extracted with dichloromethane. Combined extracts were dried over magnesium sulfate. Evaporation gave a gum (9.4 g), which was dried under high vacuum, and used as such in the next stage.

NMR (DMSO-D6) δ: 0.07 (s, 6H); 0.88 (s, 9H); 3.46 (s, 3H); 3.88 (dd, 1H); 4.25 (t, 1H); 4.49 (m, 2H); 4.61 (s, 2H); 5.06 (m, 1H); 7.36 (s, 1H); 7.46 (dm, 1H); 7.67 (t, 1H); 7.84 (dd, 1H); 7.94 (t, 1H).

(5R)-5-Azidomethyl-3-4-(4-t-butyldimethylsilyloxymethylimidazol-1-yl)-3-fluorophenyl)oxazolidin-2-one (5R)-3-(4-(4-t-Butyldimethylsilyloxymethylimidazol-1-yl)-3-fluorophenyl)-5-methane-sulfonyloxymethyloxazolidin-2-one (13.6 g) was dissolved in dry N,N-dimethyl-formnamide (110 ml). Sodium azide (3.53 g) was added, and the mixture was heated at 80° C. for 3.5 hours. The mixture was cooled, diluted with water (1.1 L) containing sodium bicarbonate (2 g), and extracted with ethyl acetate (2×800 ml). Combined organics were washed with water (2×300 ml), then brine, and dried over magnesium sulfate. The solution was evaporated to a small volume (~100 ml), and insolubles filtered. The ethyl acetate soluble material was columned on silica (100 g), eluting with ethyl acetate. Product fractions were combined and evaporated to give a gum (10.0 g).

MS (ES): 447 (MH$^+$) for $C_{20}H_{27}FN_6O_3Si$;

NMR (DMSO-D6) δ: 0.08 (s, 6H); 0.87 (s, 9H); 3.71 (dd, 1H); 3.79 (dd, 1H); 3.84 (dd, 1H); 4.20 (t, 1H); 4.61 (s, 2H); 4.93 (m, 1H); 7.36 (s, 1H); 7.46 (dm, 1H); 7.65 (t, 1H); 7.75 (dd, 1H); 7.93 (t, 1H).

N-[(5S)-3-(4-(4-t-Butyldimethylsilyloxvmethylimidazol-1-yl)-3-fluorophenyl)-2-oxooxazolidin-5-ylmethyl]acetamide To (5R)-5-azidomethyl-3-(4-(4-t-butyldimethylsilyloxymethylimidazol-1-yl)-3-fluorophenyl)oxazolidin-2-one(10.0 g) in ethyl acetate (560 ml) was added triethylamine (13.3 ml), acetic anhydride (4.5 ml), and palladium catalyst (10% on charcoal, 1.5 g), and the mixture hydrogenated at ambient temperature for 17 hours. The mixture was filtered through celite, the celite washed well with ethyl acetate, and the organic layer stirred with a saturated solution of sodium bicarbonate (100 ml) at ambient temperature for 1 hour. The organic layer was separated, dried over magnesium sulfate, and evaporated. Crude product (15 g, from two batches) was dissolved in dichloromethane and chromatographed on silica, eluting with a gradient from dichloromethane (100%) to 10% methanol in dichloromethane. Product fractions were combined to give a gum (12.3 g).

MS (ES): 462 (MH$^+$) for $C_{22}H_{31}FN_4O_4Si$; NMR(DMSO-D6) δ: 0.00 (s, 6H); 0.81 (s, 9H); 1.77 (s, 3H); 3.36 (t, 2H); 3.71 (dd, 1H); 4.08 (t, 1H); 4.54 (s, 2H): 4.77 (m, 1H); 7.29

(s, 1H); 7.38 (dm, 1H); 7.59 (t, 1H); 7.64 (dd, 1H); 7.87 (t, 1H); 8.18 (brt, 1H).

N-[(5S)-3-(3-Fluoro-4-(4-hydroxymethylimidazol-1-yl)phenyl)-2-oxooxazolidin-5-yl-methyl]acetamide N-[(5S)-3-(4-(4-t-Butyldimethylsilyloxymethylimidazol-1-yl)-3-fluorophenyl)-2-oxooxazolidin-5-ylmethyl]acetamide (6.0 g) was dissolved in a mixture of acetic acid (60 ml), THF (20 ml) and water (20 ml), and left to stir overnight at ambient temperature. Solvents were evporated at 40° in vacuo to give a gum. This was dissolved in dichloromethane (25 ml), and dry diethyl ether (100 ml) stirred in. The precipitate was triturated and stirred until properly solid, then filtered, washed with ether, and dried in vacuo to give product (3.7 g).

MS (ES): 349 (MH$^+$) for $C_{16}H_{17}FN_4O_4$; NMR (DMSO-D6) δ: 1.84 (s, 3H); 3.37 (t, 2H); 3.78 (dd, 1H); 4.16 (t, 1H); 4.39 (s, 2H); 4.77 (m, 1H); 4.97 (brs, 1H); 7.34 (s, 1 H); 7.45 (dm, 1H); 7.66 (t, 1H); 7.71 (dd, 1H); 7.91 (t, 1H); 8.22 (brt, 1H).

N-[(5S)-3-(3-Fluoro-4-(4-carboxyaldehydeimidazol-1-yl)phenyl)-2-oxooxazolidin-5-ylmethyl]acetamide N-[(5S)-3-(3-Fluoro-4-(4-hydroxymethylimidazol-1-yl)phenyl)-2-oxooxazolidin-5-ylmethyl]acetamide (5.6 g, 16 mM) and triethylamine (16.2 g, 0.16 M) were stirred in dimethylsulfoxide (40 ml) under argon at ambient temperature. A solution of pyridine-sulfur trioxide complex (7.6 g, 48 mM) in dimethylsulfoxide (40 ml) was added dropwise over 10 minutes, maintaining the temperature at ~20° C. Stirrring was continued for a further 1 hour before diluting the mixture with ice water (800 ml). Addition of isohexane (50 ml) and scratching induced crystallisation, and product was filtered off, washed with water and isohexane, and dried at 80° C. in vacuo (4 g). Purer product may be obtained by recrystallisation from acetonitrile.

MS (ESP): 347 (MH$^+$) for $C_{16}H_{15}FN_4O_4$; NMR(DMSO-D6) δ: 1.82 (s, 3H); 3.42 (t, 2H); 3.78 (dd, 1H); 4.17 (t, 1H); 4.76 (m, 1H); 7.47 (dd, 1H); 7.72, 7.74 (t overlapping dd, 2H); 8.21 (s overlapping t, 2H); 8.41 (s. 1H); 9.81 (s, 1H).

EXAMPLE 2

N-[(5S)-3-(3-Fluoro-4-(4-(E/Z-2-cyanoethenyl)imidazol-1-yl)phenyl-2-oxooxazolidin-5-ylmethyl]acetamide Diethylcyanomethylphosphonate (177 mg, 1 mM) was dissolved under argon in dry THF (4 ml), treated with potassium t-butoxide (78 mg, 0.7 mM), and stirred 5 minutes at ambient temperature. The resulting solution was added by syringe to a suspension of N-[(5S)-3-(3-fluoro-4-(4-carboxyaldehydeimidazol-1-yl)phenyl)-2-oxooxazolidin-5-ylmethyl]acetamide (173 mg, 0.5 mM) in dry THF (4 ml) and stirred at ambient temperature for 4 hours. The mixture was diluted with 5% aqueous sodium bicarbonate (20 ml), extracted with dichloromethane (30 ml), dried over magnesium sulfate and evaporated. The residue was dissolved in dichloromethane and chromatographed on a 10 g silica Mega Bond Elut® column, eluting with a gradient increasing in polarity from 0 to 10% methanol in dichloromethane. Relevant fractions were combined and evaporated to give the title product (154 mg) as a 3:1 mixture of E and Z isomers.

MS (ESP): 370 (MH$^+$) for $C_{18}H_{16}FN_5O_3$; NMR (DMSO-D6) As above except that: δ: 5.59 (d, 0.25H, J=11.8 Hz); 6.14 (d, 0.75H, J=17.4 Hz); 7.23 (d, 0.25H, J=11.8 Hz); 7.51 (d, 0.75H, J=17.4 Hz);

EXAMPLE 3

N-[(5S)-3(3-Fluoro-4-(4-(2,2-dibromoethenyl)imidazol-1-yl)phenyl)-2-oxooxazolidin-5-ylmethyl]acetamide A solution of carbon tetrabromide (332 mg, 1 mM) in dry dichloromethane (6 ml) was stirred under argon on an ice-bath. Triphenylphosphine (524 mg, 2 mM) in dichloromethane (6 ml) was added and the mixture stirred 1 hour. N-[(5S)-3-(3-Fluoro-4-(4-carboxyaldehydeimidazol-1-yl)phenyl)-2-oxooxazolidin-5-ylmethyl]acetamide (173 mg, 0.5 mM) was added as solid in one portion, and stirring continued for 1.5 hours as the temperature rose to ambient. The mixture was diluted with 5% aqueous sodium bicarbonate (20 ml), the organic phase separated, and dried over magnesium sulfate. The solution in dichloromethane was chromatographed on a 10 g silica Mega Bond Elut® column, eluting with a gradient increasing in polarity from 0 to 8% methanol in dichloromethane. Relevant fractions were combined and rechromatographed on a 10 g silica Mega Bond Elut® column, eluting with a gradient increasing in polarity from 0 to 20% isopropanol in dichloromethane. Relevant fractions were combined and evaporated to give the title product (63 mg).

MS (ESP): 501 (MH$^+$) for $C_{17}H_{15}Br_2FN_4O_3$; NMR (DMSO-D6) δ: 1.82 (s, 3H); 3.43 (t. 2H); 3.76 (dd, 1H); 4.14 (t, 1H); 4.74 (m, 1H); 7.43 (dd, 1H); 7.55 (s, 1H); 7.69, 7.74 (t overlapping dd, 2H); 7.96 (s, 1H); 8.07 (s, 1H); 8.21 (t, 1H).

EXAMPLE 4

N-[(5S)-3-(3-Fluoro-4-(4-(E/Z-2-chloroethenyl)imidazol-1-yl)phenyl)-2-oxooxazolidin-5-ylmethyl]acetamide Chloromethyltriphenylphosphonium iodide (439 mg, 1 mM) was suspended in dry THF (4 ml) and stirred under argon at ambient temperature. A solution of lithium bistrimethylsilylamide (1M in THF, 1.4 ml, 1.4 mM) was added dropwise over 5 minutes. The resulting solution of Wittig reagent was added by syringe to a suspension of N-[(5S)-3-(3-fluoro-4-(4-carboxyaldehydeimidazol- 1-yl)phenyl)-2-oxooxazolidin-5-ylmethyl]acetamide (173 mg, 0.5 mM) in dry THF (4 ml) and stirred at ambient temperature for 1.5 hours. The mixture was diluted with 5% aqueous sodium bicarbonate (20 ml), extracted with dichloromethane (30 ml), dried over magnesium sulfate and evaporated. The residue was dissolved in dichloromethane and chromatographed on a 10 g silica Mega Bond Elut® column, eluting with a gradient increasing in polarity from 0 to 10% methanol in dichloromethane. Relevant fractions were combined and rechromatographed on a 10 g silica Mega Bond Elut® column. eluting with a gradient increasing in polarity from 0 to 20% isopropanol in dichloromethane. Relevant fractions were combined and evaporated to give the title product (112 mg) as a 1:1 mixture of E and Z isomers, contaminated with N-[(5S)-3-(3-fluoro-4-(4-(2,2-dichloroethenyl)imidazol-1-yl)phenyl)-2-oxooxazolidin-5-ylmethyl]acetamide (~2:1 ratio of E/Z mixture: dichloro compound).

MS (ESP): 379 (MH$^+$) for $C_{17}H_{16}ClFN_4O_3$; NMR (DMSO-D6) δ: 1.81 (s, 3H); 3.41 (t, 2H); 3.76 (dd, 1H); 4.18 (t, 1H); 4.74 (m, 1H); 6.42 (d, 0.5H, J=7.9 Hz); 6.76 (d, 0.5H, J=7.9 Hz); 6.80 (d, 0.5H, J=13.2 Hz); 6.86 (d, 0.5H, J=13.2 Hz); 7.46 (dd, 1H); 7.68 (overlapping m, 2H); 7.87 (s, 0.5H); 7.92 (s, 0.5H); 8.02 (s, 0.5H); 8.07 (s, 0.5H); 8.21 (t, 1H).

Evidence for N-[(5S)-3-(3-fluoro-4-(4-(2,2-dichloroethenyl)imidazol-1-yl)phenyl)2-oxooxazolidin-5-ylmethyl]acetamide visible in:

MS (ESP): 413 (MH$^+$) for $C_{17}H_{15}Cl_2FN_4O_3$; NMR (DMSO-D6) δ: 7.00 (s, 1H); 7.58 (s, 1H); 7.99 (s, 1H).

EXAMPLE 5

N-[(5S)-3-(3-Fluoro-4-(4-(E/Z-2-bromoethenyl)imidazol-1-yl)phenyl)-2-oxooxazolidin-5-ylmethyl]acetamide Solid bromomethyltriphenylphosphonium bromide (436 mg, 1 mM) and potassium t-butoxide (134 mg, 1.2 mM)

were weighed under argon into a flask, and dry THF (6 ml) added by syringe. The mixture was stirred at −70° C. for 1.5 hours, warmed rapidly to ambient temperature, and added by syringe to solid N-[(5S)-3-(3-fluoro-4-(4-carboxyaldehydeimidazol-1-yl) phenyl)-2-oxooxazolidin-5-ylmethyl]acetamide (173 mg, 0.5 mM) and stirred a further 2 hours at ambient temperature. The mixture was diluted with 5% aqueous sodium bicarbonate (20 ml), extracted with dichloromethane (30 ml), dried over magnesium sulfate and evaporated. The residue was dissolved in dichloromethane and chromatographed on a 10 g silica Mega Bond Elut® column, eluting with a gradient increasing in polarity from 0 to 10% methanol in dichloromethane. Relevant fractions were combined and rechromato-graphed in the same manner. Relevant fractions were combined and evaporated to give the title product (167 mg) as a 2:3 mixture of E and Z isomers.

MS (ESP): 423 (MH$^+$) for $C_{17}H_{16}BrFN_4O_3$; NMR (DMSO-D6) δ: 1.82 (s, 3H); 3.41 (t, 2H); 3.76 (tm, 1H); 4.15 (tm, 1H); 4.74 (m, 1H); 6.57 (d, 0.6H, J=8.1 Hz); 6.92 (d, 0.4H, J=13.7 Hz); 7.06 (d, 0.4H, J=13.7 Hz); 7.18 (d, 0.6H, J=8.1 Hz); 7.43 (dm, 1H); 7.69 +7.54–7.76 (s overlapping m, 2.4H); 7.98 (s, 0.4H); 8.03 (s, 0.6H); 8.06 (s, 0.6H); 8.21 (t, 1H).

EXAMPLE 6

N-[(5S)-3-(3-Fluoro-4-(4-(E- and Z-2-chloroethenyl)imidazol-1-yl)phenyl)-2-oxooxazolidin-5-ylmethyl]acetamide Chloromethyltriphenylphosphonium iodide (439 mg, 1 mM) was suspended in dry THF (2.5 ml), stirred under nitrogen, and cooled to −75°. A solution of potassium t-butoxide (1M in THF, 1.2 ml, 1.2 mM) was added dropwise, and the mixture stirred at −70° for 1.5 hours. The resulting solution of Wittig reagent was added by syringe to a suspension of N-[(5S)-3-(3-fluoro-4-(4-carboxaldehydeimidazol-1-yl)phenyl)2-oxooxazolidin-5-ylmethyl]acetamide (173 mg, 0.5 mM) in dry THF (2.5 ml) and stirred at ambient temperature for 48 hours. The mixture was diluted with 5% aqueous sodium bicarbonate (25 ml), extracted with dichloromethane (3×10 ml), dried over magnesium sulfate and evaporated. The residue was dissolved in dichloromethane and chromatographed on a 10 g silica Mega Bond Elut® column, eluting with a gradient increasing in polarity from 0 to 4% methanol in dichloromethane. Relevant fractions were combined and evaporated to give the title compounds (160 mg) as a 2:1 mixture of Z:E isomers. Isomer separation was carried out by preparative HPLC on a Dynamax 60A 25×2 cm Si83 121C column, eluting with mixture of dichloromethane and ethanol (95:5) at 9 ml/min. Seven injections of 20 mg were made, and fractions combined to give as the first eluting component:

N-[(5S)-3-(3-Fluoro-4-(4-(E-2-chloroethenyl)imidazol-1-yl)phenyl)-2-oxooxazolidin-5-yl-methyl]acetamide (34 mg).

MS (ESP): 379 (MH$^+$) for $C_{17}H_{16}ClFN_4O_3$; NMR (DMSOd$_6$) δ: 1.82 (s, 3H), 3.41 (t, 2H); 3.76 (dd, 1H); 4.16 (t, 1H); 4.75 (m, 1H); 6.80 (d, 1H, J=13.2 Hz); 6.87 (d, 1H, J=13.2 Hz); 7.43 (dd, 1H); 7.58 (s, 1H); 7.66 (t, 1H); 7.77 (dd, 1H): 8.00 (s, 1H); 8.20 (t, 1H).

And as the second eluting component:

N-[(5S)-3-(3-Fluoro-4-(4-(Z-2-chloroethenyl)imidazol-1-yl)phenyl)-2-oxooxazolidin-5-yl-methyl]acetamide (78 mg).

MS (ESP): 379 (MH$^+$) for $C_{17}H_{16}ClFN_4O_3$; NMR (DMSOd$_6$) δ: 1.82 (s, 3H); 3.42 (t, 2H); 3.77 (dd, 1H); 4.16 (t, 1H); 4.75 (m, 1H); 6.43 (d, 1H, J=7.5 Hz); 6.76 (d, 1H, J=7.5 Hz); 7.45 (dd, 1H); 7.71 (overlapping m, 2H); 7.92 (s, 1H); 8.05 (s, 1H); 8.21 (t, 1H).

EXAMPLE 7

N-[(5S)-3-(3-Fluoro-4-(4-(E- and Z-2-bromoethenyl)imidazol-1-phenyl)-2-oxooxazolidin-5-ylmethyl]acetamide Bromomethyltriphenylphosphonium bromide (872 mg, 2 mM) was suspended in dry THF (4 ml), stirred under nitrogen, and cooled to −75°. A solution of potassium t-butoxide (1M in THF, 1.95 ml, 1.95 mM) was added dropwise, and the mixture stirred at −70° for 2.5 hours. The resulting solution of Wittig reagent was added by syringe to a suspension of N-[(5S)-3-(3-fluoro-4-(4-carboxaldehydeimidazol-1-yl)phenyl)-2-oxooxazolidin-5-ylmethyl]acetamide (346 mg, 1 mM) in dry THF (4 ml) and stirred at ambient temperature for 16 hours. The mixture was diluted with 5% aqueous sodium bicarbonate (50 ml), extracted with dichloromethane (3×30 ml), dried over magnesium sulfate and evaporated. The residue was dissolved in dichloromethane and chromatographed on a 20 g silica Mega Bond Eluto® column, eluting with a gradient increasing in polarity from 0 to 3% methanol in dichloromethane. Relevant fractions were combined and evaporated to give the title compounds (423 mg) as a 5:2 mixture of Z:E isomers.

Isomer separation was carried out by preparative HPLC on a Dynamax 60A 25×2 cm Si83 121C column, eluting with mixture of dichloromethane and ethanol (96:4) at 9 ml/min. Nine injections of 37 mg were made, and fractions combined to give as the first eluting component: N-[(5S)-3-(3-Fluoro-4-(4-(Z-2-bromoethenyl)imidazol-1-yl)phenyl)2-oxooxazolidin-5-ylmethyl]acetamide (130 mg).

MS (ESP): 423 (MH$^+$) for $C_{17}H_{16}BrFN_4O_3$; NMR (DMSOd$_6$) δ: 1.82 (s, 3H); 3.42 (t, 2H): 3.77 (dd, 1H); 4.16 (t, 1H); 4.76 (m, 1H); 6.57 (d, 1H, J=7.5 Hz); 7.17 (d, 1H, J=7.5 Hz); 7.43 (dd, 1H); 7.71 (overlapping m, 2H); 8.03 (s, 1H); 8.06 (s, 1H); 8.21 (t, 1H).

And as the second eluting component: N-[(5S)-3-(3-Fluoro-4-(4-(E-2-bromoethenyl)imidazol-1-yl)phenyl)-2-oxooxazolidin-5-ylmethyl]acetamide (75 mg).

MS (ESP): 423 (MH$^+$) for $C_{17}H_{16}BrFN_4O_3$; NMR (DMSOd$_6$) δ: 1.82 (s, 3H); 3.41 (t, 2H); 3.76 (dd, 1H); 4.15 (t, 1H); 4.77 (m, 1H); 6.91 (d, 1H, J=12.0 Hz); 7.06 (d, 1H, J=12.0 Hz); 7.44 (dd, 1H); 7.60 (s, 1H); 7.65 (t, 1H); 7.72 (dd, 1H); 7.99 (s, 1H); 8.21 (t, 1H).

EXAMPLE 8

N-[(5S)-3-(3-Fluoro-4-(4-(E/Z-2-(4-methoxyphenyl)ethenyl)imidazol-1-yl)phenyl)-2-oxooxazolidin-5-ylmethyl]acetamide Diethyl 4-methoxybenzylphosphonate (137 mg, 0.53 mM) was dissolved in dry THF (1 ml), stirred under nitrogen, and cooled to −40°. A solution of lithium bis-trimethylsilylamide (1.3M in THF, 0.41 ml, 0.53 mM) was added dropwise, and the mixture stirred at −35° for 10 minutes. The resulting solution of Wittig reagent was added by syringe to a solution of N-[(5S)-3-(3-fluoro-4-(4-carboxaldehydeimidazol-1-yl)phenyl)-2-oxooxazolidin-5-yl-methyl]acetamide (187 mg, 0.54 mM) in dry DMF (4 ml), pre-cooled to −30° and stirred for 72 hours, allowing the temperature to rise to ambient. The mixture was evaporated to an oil, dichloromethane (10 ml) added, and the resulting precipitate removed and washed with dichloromethane. The filtrate was evaporated to an oil and chromatographed on a 10 g silica Mega Bond Elut® column, eluting with a gradient increasing in polarity from 0 to 6% methanol in dichloromethane. Relevant fractions were combined and evaporated to give the title compound as a white solid after trituration with diethyl ether (20 mg) as a mixture of E and Z isomers.

MS (ESP): 451 (MH$^+$) for $C_{24}H_{23}FN_4O_4$; NMR (CDCl$_3$) δ: 2.04 (s, 3H); 3.69 (dd, 2H); 3.82 (s overlapping m, 4H); 4.08 (t, 1H); 4.82 (m, 1H); 6.14 (t, 1H). 6.89 (overlapping m, 2.5H); 7.21–7.46 (overlapping m, 6.5H); 7.69 (d, 1H); 7.77 (s, 1H).

EXAMPLE 9

N-[(5S)-3-(3-Fluoro-4-(4-(E/Z-2-(pyrid-2-yl)ethenyl)imidazo-1-yl)phenyl)-2-oxooxazolidin-5-ylmethyl]acetamide 2-Pyridylmethyltriphenylphosphonium chloride hydrochloride salt (426 mg, 1 mM) and N-[(5S)-3-(3-fluoro-4-(4-carboxaldehydeimidazol-1-yl)phenyl)-2-oxooxazolidin-5-yl-methyl]acetamide (173 mg, 0.5 mM) were suspended in dry THF (5 ml), stirred under nitrogen, and cooled to –70°. A solution of potassium t-butoxide (1M in THF, 1.5 ml, 1.5 mM) was added dropwise, and the mixture stirred 4 hours, allowing the temperature to rise to ambient. The mixture was diluted with 5% aqueous sodium bicarbonate (25 ml), extracted with dichloromethane (3×10 ml), dried over magnesium sulfate and evaporated. The residue was dissolved in dichloromethane and chromatographed on a 10 g silica Mega Bond Elut® column, eluting with a gradient increasing in polarity from 0 to 4% methanol in dichloromethane. Relevant fractions were combined and evaporated to give the title compound (135 mg) as a 4:1 mixture of E:Z isomers.

MS (ESP): 422 (MH$^+$) for $C_{22}H_{20}FN_5O_3$; NMR (DMSOd$_6$) δ: 1.88 (s, 3H); 3.48 (t, 2H); 3.83 (dd, 1H); 4.23 (t, 1H); 4.83 (m, 1H); 6.55 (d, 0.2H, J=13.1 Hz); 6.71 (d, 0.2H, J=13.1 Hz); 7.25 (m, 1H); 7.31 (d, 0.8H, J=15.5 Hz); 7.52 (m, 2H); 7.62 (d, 0.8H, J=15.5 Hz); 7.79 (m, 4H); 8.09 (s, 0.2H); 8.11 (s, 0.8H); 8.31 (t, 1H); 8.57 (m, 1H).

EXAMPLE 10

N-[(5S)-3-(3-Fluoro-4-(4-(Z-2-(2,4-difluorophenyl)ethenyl)imidazol-1-yl)phenyl)-2-oxooxazolidin-5-ylmethyl]acetamide 2,4-Difluorophenylmethyltriphenylphosphonium bromide (469 mg, 1 mM) and N-[(5S)-3-(3-fluoro-4-(4-carboxaldehydeimidazol-1-yl)phenyl)-2-oxooxazolidin-5-ylmethyl]acetamide (173 mg, 0.5 mM) were suspended in dry THF (3 ml), stirred under nitrogen, and cooled to –70°. A solution of potassium t-butoxide (1M in THF, 1 ml, 1 mM) was added dropwise, and the mixture stirred 4 hours, allowing the temperature to rise to ambient. The mixture was diluted with 5% aqueous sodium bicarbonate (25 ml), extracted with dichloromethane (3×15 ml), dried over magnesium sulfate and evaporated. The residue was dissolved in dichloro-methane and chromatographed on a 10 g silica Mega Bond Elut® column, eluting with a gradient increasing in polarity from 0 to 2% methanol in dichloromethane. Relevant fractions were combined and evaporated to give the title compound (183 mg) as the Z isomer.

MS (ESP): 457 (MH$^+$) for $C_{23}H_{19}F_3N_4O_3$; NMR (DMSOd$_6$) δ: 1.82 (s, 3H); 3.42 (t, 2H); 3.76 (dd, 1H); 4.14 (t, 1H); 4.75 (m, 1H); 6.39 (d, 1H, J=12.4 Hz); 6.60 (d, 1H, J=12.4 Hz); 7.02 (td, 1H); 7.18 (m, 1H); 7.37 (s, 1H); 7.42 (dd, 1H); 7.62 (t, 1H); 7.73 (dd, 1H); 7.92, 7.96 (s overlapping m, 2H); 8.31 (t, 1H).

The starting phosphonium salt was prepared as follows:

1-Bromomethyl-2,4-difluorobenzene (1 g, 4.83 mM) and triphenylphosphine (1.27 g, 4.85 mM) wre added to DMF (10 ml) and stirred under reflux for 18 hours. After cooling, the solvent was removed, and the residue treated with diethyl ether (50 ml) to precipitate the product (2.11 g).

MS (ESP): 389 (M$^+$) for $C_{25}H_{20}F_2P$; NMR (DMSOd$_6$) δ: 5.14 (d, 2H); 6.99 (td, 1H); 7.11 (td, 1H); 7.46 (td, 1H); 7.46 (td, 1H); 7.46 (m, 12H); 7.92 (m, 3H).

EXAMPLE 11

N-[(5S)-3-(3-Fluoro-4-(4-(E-2-(Pyrid-2-yl)ethenyl)imidazol-1-yl)phenyl)-2-oxooxazolidin-5-ylmethyl]acetamide 2-Pyridylmethyltriphenylphosphonium chloride hydrochloride salt (1.7 g, 4 mM) and N-[(5S-3-(3-fluoro-4-(4-carboxaldehydeimidazol-1-yl)phenyl)-2-oxooxazolidin-5-yl-methyl]acetamide (692 mg, 2 mM) were suspended in dry THF (15 ml), stirred under nitrogen, and cooled to –50°. A solution of potassium t-butoxide (1M in THF, 8 ml, 8 mM) was added dropwise, and the mixture stirred at –40° for 1 hour. The temperature was then allowed to rise to ambient, and the mixture stirred at this temperature for 18 hours. The mixture was diluted with water (75 ml), extracted with ethyl acetate (3×50 ml), dried over magnesium sulfate and evaporated. The residue was dissolved in 1% methanol in dichloro-methane and purified by flash chromatography on silica, eluting with a gradient increasing in polarity from 1 to 4% methanol in dichloromethane. Relevant fractions were combined and evaporated to give the title compound (396 mg) as the E isomer.

MS (ESP): 422 (MH$^+$) for $C_{22}H_{20}FN_5O_3$; NMR (DMSOd$_6$) δ: 1.82 (s, 3H); 3.42 (t, 2H); 3.78 (dd, 1H); 4.16 (t, 1H); 4.14 (t, 1H); 4.76 (m, 1H); 7.18 (dd, 1H); 7.23 (d, 1H, J=15.8 Hz); 7.45 (t overlapping m, 2H); 7.56 (d, 1H, J=15.8 Hz); 7.69 (t overlapping m, 3H); 7.76 (s, 1H); 8.05 (s, 1H); 8.22 (t, 1H); 8.52 (d, 1H).

A portion of the above compound (96 mg) was dissolved in hot ethanol, cooled to ambient temperature, and hydrochloric acid (3.8M in ethanol, 0.5 ml) added. The resulting precipitate was filtered to give the dihydrochloride salt of the title compound (solubility in water approximately 10 mg/ml).

Elemental analysis: Found: C, 50.8; H, 4.3; N, 13.2; Cl, 13.3%. Calc for $C_{22}H_{20}FN_5O_3 \cdot 2HCl \cdot 1.3H_2O$: C, 51.0; H, 4.8; N, 13.5; Cl, 13.7%; NMR(DMSOd$_6$) δ: 1.82(s, 3H); 3.42(t, 2H); 3.81 (dd, 1H); 4.18(t, 1H); 4.77(m, 1H); 7.48 (dd, 1H); 7.54 (d, 1H, J=15.9 Hz); 7.71 (t, 1H); 7.77 (t overlapping m, 2H); 7.95 (d, 1H, J=15.8 Hz); 8.08 (s, 1H); 8.17 (d, 1H); 8.42 (t, 1H); 8.48 (t, 1H); 8.62 (s, 1H); 8.67 (d, 1H).

EXAMPLE 12

N-[(5S)-3-(3-Fluoro-4-(4-(E/Z-2-(1-oxo-pyrid-2-yl)ethenyl)imidazol-1-yl)phenyl)-2-oxooxazolidin-5-ylmethyl]acetamide N-[(5S)-3-(3-Fluoro-4-(4-(E-2-(pyrid-2-yl)ethenyl)imidazol-1-yl)phenyl)-2-oxooxazolidin-5-ylmethyl]acetamide (189 mg, 0.45 mM) was dissolved in a mixture of dichloromethane (10 ml) and methanol (5 ml), and cooled to 0° with stirring. A solution of 3-chloroperoxybenzoic acid (50%, 232 mg, 0.68 mM) in dichloromethane (6 ml) was added, and the mixture stirred for 24 hours. Solvent was evaporated, and the residue dissolved in dichloromethane and chromatographed on a 10 g silica Mega Bond Elut® column, eluting with a gradient increasing in polarity from 3.5 to 10% methanol in dichloromethane. Relevant fractions were combined and evaporated to give the title compound (56 mg) as a solid after trituration with diethyl ether, as a 5:1 mixture of E:Z isomers.

MS (ESP): 438 (MH$^+$) for $C_{22}H_{20}FN_5O_4$; NMR (DMSOd$_6$) δ: 1.82 (s, 3H); 3.44 (t, 2H); 3.77 (dd, 1H); 4.16 (t, 1H); 4.75 (m, 1H); 6.61 (d, 0.2H, J=12.0 Hz); 6.72 (d, 0.2H, J=12.0 Hz); 7.22 (t, 1H); 7.28 (t, 1H); 7.46 (dd, 1H); 7.63–7.84 (overlapping m, 5.6H); 8.02 (s, 0.2H); 8.09 (s, 0.8H); 8.22 (overlapping m, 2H).

EXAMPLE 13

N-[(5S)-3-(3-Fluoro-4-(4-ethynylimidazol-1-yl) phenyl)-2-oxooxazolidin-5-ymethyl]acetamide Bromomethyltriphenylphosphonium bromide (436 mg, 1 mM) was suspended in dry THF (2.5 ml). stirred under nitrogen, and cooled to −75°. A solution of potassium t-butoxide (1M in THF, 1.2 ml, 1.2 mM) was added dropwise, and the mixture stirred at −70° for 1.5 hours. The resulting solution of Wittig reagent was added by syringe to a suspension of N-[(5S)-3-(3-fluoro-4-(4-carboxaldehydeimidazol-1-yl)phenyl)-2-oxooxazolidin-5-ylmethyl]acetamide (173 mg, 0.5 mM) in dry THF (2.5 ml) and stirred at ambient temperature for 16 hours. The mixture was diluted with 5% aqueous sodium bicarbonate (25 ml), extracted with dichloromethane (3×10 ml), dried over magnesium sulfate and evaporated. The residue was dissolved in dichloromethane and chromatographed on a 20 g silica Mega Bond Elut® column, eluting with a gradient increasing in polarity from 0 to 3% methanol in dichloromethane. Relevant fractions were combined and evaporated to give the title compound in a mixture with the bromovinyl compounds of Example 7.

The mixture was separated by preparative HPLC on a Dynamax 60A 25×2 cm Si83 121 C column, eluting with mixture of dichloromethane and ethanol (95:5) at 9 ml/min. Seven injections of 20 mg were made, and fractions combined to give title compound as the first eluting component.

MS (ESP): 342 (MH$^+$) for $C_{17}H_{15}FN_4O_3$; NMR (DMSOd$_6$) δ: 1.81 (s, 3H); 3.41 (t, 2H); 3.76 (dd, 1H); 4.16 (s, 1H); 4.16 (t, 1H); 4.76 (m, 1H); 7.44 (dd, 1H); 7.66 (t, 1H); 7.73 (dd, 1H); 7.87 (s, 1H); 7.99 (s, 1H); 8.21 (t, 1H).

EXAMPLE 14

N-[(5S)-3-(3-Fluoro-4-(4-(E-2-(pyrid-4-yl)ethenyl) imidazol-1-yl)phenyl)-2-oxooxazolidin-5-ylmethyl] acetamide A mixture of 4-picoline (465 mg, 5 mM), N-[(5S)-3-(3-fluoro-4-(4-carboxaldehydeimidazol-1-yl)phenyl)-2-oxooxazolidin-5-ylmethyl]acetamide (173 mg, 0.5 mM), acetic anhydride (510 mg, 5 mM) and acetic acid (300 mg, 5 mM) was heated and stirred under nitrogen at 95° for 16 hours. The mixture was diluted with 5% aqueous sodium bicarbonate (20 ml), extracted with dichloromethane (3×10 ml), dried over magnesium sulfate and evaporated. The residue was dissolved in dichloromethane and chromatographed on a 10 g silica Mega Bond Elut® column, eluting with a gradient increasing in polarity from 0 to 20% methanol in dichloromethane. Relevant fractions were combined and evaporated to give the title compound (19 mg) after trituration with hot ethyl acetate.

MS (ESP): 422 (MH$^+$) for $C_{22}H_{20}FN_5O_3$; NMR (DMSOd$_6$) δ: 1.82 (s, 3H); 3.42 (t, 2H); 3.78 (dd, 1H); 4.16 (t, 1H); 4.76 (m, 1H); 7.15 (d, 1H, J=15 Hz); 7.42 (d, 1H, J=15 Hz): 7.48 (overlapping m, 3H); 7.70 (t, 1H); 7.74 (overlapping m, 2H); 8.07 (s, 1H); 8.21 (t, 1H); 8.49 (d, 2H).

EXAMPLE 15

N-[(5S)-3-(3-Fluoro-4-(4-(E/Z-2-(pyrid-4-yl) ethenyl)imidazol-1-yl)phenyl)2-oxooxazolidin-5-ylmethyl]acetamide 4-Pyridylmethyltriphenylphosphonium chloride hydrochloride salt (426 mg, 1 mM) and N-[(5S)-3-(3-fluoro-4-(4-carboxaldehydeimidazol-1-yl)phenyl)-2-oxooxazolidin-5-yl-methyl]acetamide (173 mg, 0.5 mM) were suspended in dry THF (3 ml), stirred under nitrogen, and cooled to −70°. A solution of potassium t-butoxide (1M in THF, 2 ml, 2 mM) was added dropwise, and the mixture stirred for 2 hours, allowing the temperature to rise to ambient. The mixture was diluted with 5% aqueous sodium bicarbonate (25 ml), extracted with dichloromethane (3×15 ml), dried over magnesium sulfate and evaporated. The residue was dissolved in dichloromethane and chromatographed on a 10 g silica Mega Bond Elut® column, eluting with a gradient increasing in polarity from 0 to 3.5% methanol in dichloromethane. Relevant fractions were combined and evaporated to give the title compounds (84 mg) as a 1:1 mixture of E:Z isomers.

MS (ESP): 422 (MH$^+$) for $C_{22}H_{20}FN_5O_3$; NMR (CDCl$_3$) δ: 2.04 (s, 3H); 3.68 (dd, 2H); 3.85 (dd, 1H); 4.08 (dd, 1H); 4.83 (m, 1H); 6.37 (t, 1H); 6.45 (d, 0.5H, J=12.5 Hz); 6.66 (d, 0.5H, J=12.5 Hz); 6.99 (s, 0.5H); 7.22–7.50 (overlapping m, 5H); 7.72 (m, 2H); 7.81 (s, 0.5H); 8.54 (m, 2H).

The starting phosphonium salt was prepared as follows:

4-Chloromethylpyridine hydrochloride (1 g, 6.1 mM) and triphenylphosphine (1.6 g, 6.11 mM) were added to DMF (10 ml) and stirred under reflux for 18 hours. After cooling, the solvent was removed, and the residue treated with diethyl ether (50 ml) to precipitate the product (2.52 g).

MS (ESP): 354 (M$^+$) for $C_{24}H_{21}NP$; NMR (DMSOd$_6$) δ: 5.33 (d, 2H); 6.98 (m, 2H); 7.73 (m, 12H): 7.89 (m, 3H); 8.40 (d, 2H).

EXAMPLE 16

N-[(5S)-3-(3-Fluoro-4-(4-(2,2-difluoroethenyl) imidazol-1-yl)phenyl)-2-oxooxazolidin-5-ylmethyl] acetamide Triphenylphosphine (288 mg, 1.09 mM), sodium chlorodifluoroacetate (229 mg, 1.5 mM), and N-[(5S)-3-(3-fluoro-4-(4-carboxaldehydeimidazol-1-yl)phenyl)-2-oxooxazolidin-5-yl-methyl]acetamide (173 mg, 0.5 mM), were suspended in dry DMF (1 ml) and heated under nitrogen at 135°. After the vigorous gas evolution had subsided, heating was continued for 0.5 hours. The mixture was cooled, diluted with 5% aqueous sodium bicarbonate (30 ml), extracted with dichloromethane (3×10 ml), dried over magnesium sulfate and evaporated. The residue was dissolved in dichloromethane and chromatographed on a 10 g silica Mega Bond Elut® column, eluting with a gradient increasing in polarity from 0 to 10% methanol in dichloromethane. Relevant fractions were combined and evaporated to give the title compound (8 mg).

MS (ESP): 381 (MH$^+$) for $C_{17}H_{15}F_3N_4O_3$; NMR (DMSOd$_6$) δ: 1.81 (s, 3H); 3.42 (t, 2H); 3.77 (dd, 1H); 4.15

(t, 11H); 4.75 (m, 1H); 5.64 (dd, 1H); 7.43 (dd, 1H); 7.49 (s, 1H); 7.67 (t, 1H); 7.73 (dd, 1H); 8.01 (s, 1H); 8.21 (t, 1H).

EXAMPLE 17

The following illustrate representative pharmaceutical dosage forms containing the compound of formula (I), or a pharmaceutically-acceptable salt thereof (hereafter compound X), for therapeutic or prophylactic use in humans:

(a)

| Tablet I | mg/tablet |
|---|---|
| Compound X. | 100 |
| Lactose Ph. Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph. Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph. Eur. | 339 |
| Croscarmellose sodium | 100 |
| Magnesium stearate | 1. |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula (I):

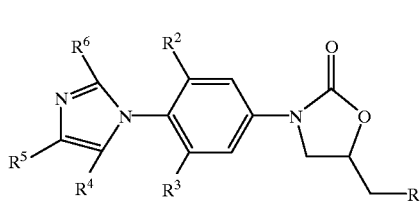

wherein:
$R^1$ is chloro, fluoro, (1–4C)alkanesulfonyloxy, azido, or of the formula —NHC(=O)$R^a$ wherein $R^a$ is hydrogen, (1–4C)alkoxy, chloromethyl, dichloromethyl, cyanomethyl, methoxymethyl, acetylmethyl or (1–4C)alkyl;

$R^2$ and $R^3$ are independently hydrogen or fluoro;

$R^4$ is hydrogen, (1–4C)alkyl, halo or trifluoromethyl;

$R^5$ and $R^6$ are independently selected from hydrogen, (1–4C)alkyl, halo, trifluoromethyl, an acetylene of the formula -≡-H or -≡-(1–4C)alkyl, and a group of the formula (IA)

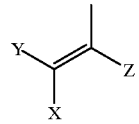

wherein Z is hydrogen or (1–4C)alkyl; X and Y are independently selected from hydrogen, (1–4C)alkyl, halo, cyano, nitro, —S(O)$_n$(1–4C)alkyl (wherein n is 0, 1 or 2), aminosulfonyl, (1–4C)alkylaminosulfonyl, di-(1–4C)alkylaminosulfonyl, trifluoromethyl, pentafluoroethyl, (1–4C)alkanoyl, carbamoyl, N-(1–4C)alkylcarbamoyl, and N,N-di-(1–4C) alkylcarbamoyl; or one of X and Y is selected from the above list and the other is selected from phenyl, phenylcarbonyl, —S(O)$_n$-phenyl (wherein n is 0, 1 or 2), N-(phenyl)carbamoyl, phenylaminosulfonyl, heteroaryl, heteroarylcarbonyl, —S(O)$_n$-heteroaryl (wherein n is 0, 1 or 2), N-(heteroaryl)carbamoyl and heteroarylaminosulfonyl; wherein any phenyl group above may be optionally substituted by up to three substituents independently selected from (1–4C)alkyl, cyano, trifluoromethyl, nitro, halo and (1–4C) alkylsulfonyl; wherein any heteroaryl group in X and Y may be optionally substituted on an available carbon atom by (1–4C)alkyl, and optionally substituted on a suitable nitrogen atom by oxo (to form an N-oxide); provided that X, Y and Z do not define a (2–4C)alkenyl group and provided that at least one of $R^5$ and $R^6$ is a group of the formula (IA) or an acetylene of the formula -≡-H or -≡-(1–4C)alkyl;

or a pharmaceutically acceptable salt thereof.

2. A compound of the formula (I), as claimed in claim 1, wherein $R^1$ is acetamido; one of $R^2$ and $R^3$ is hydrogen and the other is fluoro; $R^4$ and $R^6$ are hydrogen; $R^5$ is a group of the formula (IA) wherein Z is hydrogen and X and Y are independently selected from halo, cyano, nitro and (1–4C) alkanoyl.

3. A compound of the formula (I), as claimed in claim 1, wherein $R^1$ is acetamido; one of $R^2$ and $R^3$ is hydrogen and the other is fluoro; $R^4$ and $R^6$ are hydrogen; $R^5$ is a group of the formula (IA) wherein Z is hydrogen, one of X and Y is hydrogen and the other is selected from halo, cyano, nitro and (1–4C)alkanoyl.

4. A compound of the formula (I), as claimed in claim 1, wherein $R^1$ is acetamido; one of $R^2$ and $R^3$ is hydrogen and the other is fluoro; $R^4$ and $R^6$ are hydrogen; $R^5$ is a group of the formula (IA) wherein Z is hydrogen, one of X and Y is hydrogen and the other is selected from phenyl, phenylcarbonyl, —S(O)$_n$-phenyl (wherein n is 0, 1 or 2), N-(phenyl)carbamoyl, phenylaminosulfonyl, heteroaryl, heteroarylcarbonyl, —S(O)$_n$-heteroaryl (wherein n is 0, 1 or 2), N-(heteroaryl)carbamoyl and heteroarylarninosulfonyl; wherein any phenyl group above may be optionally substituted by up to three substituents independently selected from (1–4C)alkyl, cyano, trifluoromethyl, nitro, halo and (1–4C)alkylsulfonyl; and wherein any heteroaryl group may be optionally substituted on an available carbon atom by (1–4C)alkyl, and optionally substituted on a suitable nitrogen atom by oxo (to form an N-oxide); or a pharmaceutically acceptable salt thereof.

5. A compound of the formula (I), as claimed in claim 1, selected from the following mixtures of E- and Z-isomers, and the individual E- and Z-isomers contained in the mixtures:

N-[(5S)-3-(3-Fluoro-4-(4-(E/Z-2-cyanoethenyl)imidazol-1-yl)phenyl)-2-oxooxazolidin-5-ylmethyl]acetamide;

N-[(5S)-3-(3-Fluoro-4-(4-(2,2-dibromoethenyl)imidazol-1-yl)phenyl)-2-oxooxazolidin-5-ylmethyl]acetamide;

N-[(5S)3-(3-Fluoro-4-(4-(E/Z-2-bromoethenyl)imidazol-1-yl)phenyl)-2-oxooxazolidin-5-ylmethyl]acetamide;

N-[(5S)-3-(3-Fluoro-4-(4-(2,2-dichloroethenyl)imidazol-1-yl)phenyl)-2-oxooxazolidin-5-ylmethyl]acetamide; and N-[(5S)-3-(3-Fluoro-4-(4-(E/Z-2-chloroethenyl)imidazol-1-yl)phenyl)-2-oxo-5-oxazolidinylmethyl]acetamide.

6. A compound of the formula (I), as claimed in claim 1, selected from the following mixtures of E- and Z-isomers, and the individual E- and Z-isomers contained in the mixtures:

N-[(5S)-3-(3-Fluoro-4-(4-(E/Z-2-(pyrid-4-yl)ethenyl)imidazol-1-yl)phenyl)-2-oxooxazolidin-5-ylmethyl]acetamide;

N-[(5S)-3-(3-Fluoro-4-(4-(E/Z-2-(1-oxo-pyrid-2-yl)ethenyl)imidazol-1-yl)phenyl)-2-oxooxazolidin-5-ylmethyl]acetamide;

N-[(5S)-3-(3-Fluoro4-(4-(E/Z-2-(2,4-difluorophenyl)ethenyl)imidazol-1-yl)phenyl)-2-oxooxazolidin-5-ylmethyl]acetamide;

N-[(5S)-3-(3-Fluoro-4-(4-(E/Z-2-(pyrid-2-yl)ethenyl)imidazol-1-yl)phenyl)-2-oxooxazolidin-5-ylmethyl]acetamide; and N-[(5S)-3-(3-Fluoro-4(4-(E/Z-2-(4-methoxyphenyl)ethenyl)imidazol-1-yl)phenyl)-2-oxooxazolidin-5-ylmethyl]acetamide; or a pharmaceutically acceptable salt of a compound containing a pyridyl group with an unsubstituted nitrogen atom.

7. A pharmaceutical composition which comprises a compound of the formula (I), as claimed in claim 1, or a pharmaceutically-acceptable salt thereof, and a pharmaceutically-acceptable diluent or carrier.

8. A method for producing an antibacterial effect in a warm blooded animal, in need of such treatment, which comprises administering to said animal an effective amount of a compound of the present invention, or a pharmaceutically-acceptable salt thereof, as claimed in claim 1.

* * * * *